United States Patent
Rohloff et al.

(10) Patent No.: US 9,938,314 B2
(45) Date of Patent: Apr. 10, 2018

(54) CYTIDINE-5-CARBOXAMIDE MODIFIED NUCLEOTIDE COMPOSITIONS AND METHODS RELATED THERETO

(71) Applicant: SomaLogic, Inc., Boulder, CO (US)

(72) Inventors: John Rohloff, Boulder, CO (US); Nebojsa Janjic, Boulder, CO (US); Bharat Nathu Gawande, Lafayette, CO (US)

(73) Assignee: SOMALOGIC, INC., Boulder, CO (US)

( * ) Notice: Subject to any disclaimer, the term of this patent is extended or adjusted under 35 U.S.C. 154(b) by 113 days.

(21) Appl. No.: 14/917,056

(22) PCT Filed: Nov. 19, 2014

(86) PCT No.: PCT/US2014/066328
§ 371 (c)(1),
(2) Date: Mar. 7, 2016

(87) PCT Pub. No.: WO2015/077292
PCT Pub. Date: May 28, 2015

(65) Prior Publication Data
US 2016/0215013 A1 Jul. 28, 2016

Related U.S. Application Data

(60) Provisional application No. 61/907,274, filed on Nov. 21, 2013.

(51) Int. Cl.
C07H 19/06 (2006.01)
C07H 1/00 (2006.01)
C07H 21/00 (2006.01)
C12Q 1/68 (2018.01)

(52) U.S. Cl.
CPC ............ *C07H 19/06* (2013.01); *C07H 1/00* (2013.01); *C07H 21/00* (2013.01); *C12Q 1/6811* (2013.01)

(58) Field of Classification Search
None
See application file for complete search history.

(56) References Cited

U.S. PATENT DOCUMENTS

| | | | |
|---|---|---|---|
| 4,267,171 A | 5/1981 | Bergstrom et al. | |
| 4,415,732 A | 11/1983 | Caruthers et al. | |
| 4,594,339 A | 6/1986 | Lopez et al. | |
| 4,711,955 A | 12/1987 | Ward | |
| 4,725,677 A | 2/1988 | Koster | |
| 4,828,979 A | 5/1989 | Kelvan et al. | |
| 4,948,882 A | 8/1990 | Ruth | |
| 4,997,818 A | 3/1991 | McCaffrey et al. | |
| 5,023,243 A | 6/1991 | Tullis | |
| 5,047,519 A | 9/1991 | Hobbs, Jr. et al. | |
| 5,093,232 A | 3/1992 | Urdea et al. | |
| 5,118,672 A | 6/1992 | Schinazi et al. | |
| 5,134,066 A | 7/1992 | Rogers et al. | |
| 5,138,045 A | 8/1992 | Cook et al. | |
| 5,428,149 A | 6/1995 | Eaton | |
| 5,576,429 A | 11/1996 | Johansson et al. | |
| 5,580,972 A | 12/1996 | Tu | |
| 5,582,981 A | 12/1996 | Toole et al. | |
| 5,591,843 A | 1/1997 | Eaton et al. | |
| 5,595,877 A | 1/1997 | Gold et al. | |
| 5,596,091 A | 1/1997 | Switzer | |
| 5,633,361 A | 5/1997 | Eaton et al. | |
| 5,645,985 A | 7/1997 | Froehler | |
| 5,658,738 A | 8/1997 | Nadeau et al. | |
| 5,660,985 A | 8/1997 | Pieken et al. | |
| 5,719,273 A | 2/1998 | Tu et al. | |
| 5,801,154 A | 9/1998 | Baracchini et al. | |
| 5,817,785 A | 10/1998 | Gold et al. | |
| 5,840,867 A | 11/1998 | Toole et al. | |
| 5,945,527 A | 8/1999 | Tu et al. | |
| 5,958,691 A | 9/1999 | Pieken | |
| 6,020,483 A | 2/2000 | Beckvermit et al. | |
| 6,030,776 A | 2/2000 | Eaton et al. | |
| 6,175,001 B1 | 1/2001 | Barbas et al. | |
| 6,184,364 B1 | 2/2001 | Pieken et al. | |
| 6,344,318 B1 | 2/2002 | Gold et al. | |
| 6,355,787 B1 | 3/2002 | Beckvermit et al. | |
| 6,716,583 B2 | 4/2004 | Gold et al. | |
| 7,094,770 B2 | 8/2006 | Watanabe et al. | |
| 7,855,054 B2 | 12/2010 | Schneider et al. | |
| 7,947,447 B2 | 5/2011 | Zichi et al. | |
| 8,404,830 B2 | 3/2013 | Zichi et al. | |
| 9,163,056 B2 | 10/2015 | Rohloff et al. | |
| 9,382,533 B2 | 7/2016 | Zichi et al. | |

(Continued)

FOREIGN PATENT DOCUMENTS

JP Hei 5-500799 A 2/1993
JP 2000-327694 A 11/2000

(Continued)

OTHER PUBLICATIONS

IPRP dated May 24, 2016 in PCT/US2014/066328.
You, Qidong et al. (Jan. 31, 2004) Medicinal Chemistry, Chemical Industry Press, pp. 32-34, with Office Action dated Mar. 31, 2016 in Chinese Patent Application No. 201180028946.3 to show relevance.
Agathocleous and Shaw (1991) J. Chem. Soc. Perkin Trans. 1: 2317-2321, "Purines, pyrimidines and imidazoles. Part 66. New Synthesis of some uridine and N-alkoxycarbonyl 5-carboxyamides, N-carbomoyl 5-carboxyamides and 5-carboxyamides".

(Continued)

*Primary Examiner* — Traviss C McIntosh, III
(74) *Attorney, Agent, or Firm* — Swanson & Bratschun, L.L.C.

(57) ABSTRACT

Described herein are 5-position modified cytosine nucleotides and nucleosides as well as phosphoramidites and triphosphates derivatives thereof. Further provided are methods of making and using the same, and compositions and uses of the modified nucleosides as part of a nucleic acid molecule (e.g., aptamer).

13 Claims, 1 Drawing Sheet

(56) References Cited

U.S. PATENT DOCUMENTS

| | | | |
|---|---|---|---|
| 9,404,919 | B2 | 8/2016 | Schneider et al. |
| 2003/0144231 | A1 | 7/2003 | Wengel et al. |
| 2005/0130195 | A1 | 6/2005 | Fujihara et al. |
| 2005/0227225 | A1 | 10/2005 | Krevolin |
| 2005/0288244 | A1 | 12/2005 | Manoharan et al. |
| 2006/0057573 | A1 | 3/2006 | Gold et al. |
| 2007/0041901 | A1 | 2/2007 | Diener et al. |
| 2007/0166741 | A1 | 7/2007 | Heil et al. |
| 2008/0194502 | A1 | 8/2008 | Dellinger et al. |
| 2009/0004667 | A1 | 1/2009 | Zichi et al. |
| 2009/0098549 | A1 | 4/2009 | Schneider et al. |
| 2010/0285479 | A1 | 11/2010 | Jenison |
| 2010/0317723 | A1 | 12/2010 | Lee et al. |
| 2011/0082286 | A1 | 4/2011 | Zichi et al. |
| 2011/0136099 | A1 | 6/2011 | Schneider et al. |
| 2011/0275794 | A1 | 11/2011 | Rohloff et al. |
| 2012/0264117 | A1 | 10/2012 | Sanders et al. |
| 2013/0131141 | A1 | 5/2013 | Khovorova et al. |
| 2014/0058076 | A1 | 2/2014 | Rohloff et al. |
| 2014/0249043 | A1 | 9/2014 | Schneider et al. |
| 2015/0197753 | A1 | 7/2015 | Zicki et al. |
| 2015/0376223 | A1 | 12/2015 | Rohloff et al. |
| 2016/0355540 | A1 | 12/2016 | Rohloff et al. |

FOREIGN PATENT DOCUMENTS

| | | |
|---|---|---|
| JP | 2004-238353 A | 8/2004 |
| JP | 2013-523887 | 6/2013 |
| WO | WO 1990/15065 | 12/1990 |
| WO | WO 1991/13900 | 9/1991 |
| WO | WO 2006/063717 | 6/2006 |
| WO | WO 2008/078180 A2 | 7/2008 |
| WO | WO 2008/104408 | 9/2008 |
| WO | WO 2008/137776 A2 | 11/2008 |
| WO | WO 2011/032143 | 3/2011 |
| WO | WO 2011/109642 | 9/2011 |
| WO | WO 2011/129494 A1 | 10/2011 |
| WO | WO 2011/130065 A1 | 10/2011 |
| WO | WO 2012/061810 | 5/2013 |

OTHER PUBLICATIONS

Agris et al. (1995) Biochimie 771(1-2):125-134, "Site-selected introduciton of modified purine and pyrimidine ribonucleosides into RNA by automated phosphoramidite chemistry".

Bergstrom and Ruth (1976) J. Amer. Chem. Soc. 98(6): 1587-1589, "Synthesis of C-5 substituted pyrimidine nucleosides via organopalladium intermediates".

Bergstrom et al. (1982) J. Org. Chem. 47(11): 2174-2178, "Pyrido[2,3-d]pyrimidine nucleosides. Synthesis via cyclization of C-5-substituted cytidines".

Bier and Fürste, (Feb. 1997) EXS 80:97-120, "Nucleic Acid based sensors".

Bigge and Mertes (1981) J. Org. Chem. 46(10): 1994-1997, "A palladium-catalyzed coupling reaction and a photolytic reaction for the direct synthesis of 5-arylpyrimidine nucleotides".

Brodsky (2002) Mol. Cell. Proteomics 1(12):922-929, "A Microbead-based System for Identifying and Characterizing RNA-Protein Interactions by Flow Cytometry".

Crisp (1989) Synthetic Communications 19: 2117-2123, "Synthesis of 5-alkenyl-2' deoxyuridines via organostannanes".

Crisp and Flynn (1990) Tetrahedron Letters 31(9):1347-1350, "Palladium-catalysed coupling of uridine triflate with organostannanes".

Crouch and Eaton (1994) Nucleosides & Nucleotides 13(4): 939-944, "Synthesis of 2'deoxyuridine nucleosides with appended 5-position carbonyl cross-linking groups".

Dewey et al. (1995) J. Am. Chem. Soc. 117: 8474-8475, "New Uridine Derivatives for Systematic Evolution of RNA Ligands by Exponential Enrichment".

DiDonato (2006) "Dissertation" University of North Carolina, Raleigh.

Eaton et al. (1997) Bioorganic & Medicinal Chemistry 5(6):1087-1096, "Post-SELEX Combinatorial Optimization of Aptamers".

Eaton et al. (1997) Current Opinion in Chemical Biology 1:10-16, "The joys of in vitro selection: chemically dressing oligonucleotides to satiate protein targets".

El Safadi et al. (2010) J. Med. Chem. 53:1534-1545, "5-Modified-2'-dU and 2'-dC as Mutagenic Anti HIV-1 Proliferation Agents: Synthesis and Activity".

EP Search report dated Dec. 1, 2009 in EP application serial No. 08782010.6.

EP Search report dated Feb. 22, 2010 in EP application serial No. 09012809.1.

European Search Report dated Sep. 25, 2013 in EP 11769451.3.

Gold et al. (Dec. 7, 2010) PLOS One 5(12):1-17, (e15004), "Aptamer-Based Multiplexed Proteomic Technology for Biomarker Discovery".

Goodchild et al. (1983) J. Med. Chem. 26(9): 1252-1257, "Structural Requirements of Olefinic 5-Substituted Deoxyuridines for Antiherpes Activity".

Hobbs et al. (1973) Biochemistry 12(25): 5138-5145, "Polynucleotides Containing 2'-Amino-2'deoxyribose and 2'-Azido-2'deoxyribose".

Holmes et al. (2005) "Syntheses and Oligonucleotide Incorporation of Nucleoside Analogues Containing Pendant Imidazolyl or Amino Functionalities—the Search for Sequence-Specific Artifical Ribonucleases" Eur. J. Org. pp. 5171-5183.

Holy (1972) Collection Czechoslov. Chem. Commun. 37: 1555-1576, "Nucleic acid components and their analogues. CXLVII. Preparation of 5-ethoxycarbonyluridine, 5-carboxyuridine and their nucleotide derivatives".

Ikehara and Tada (1968) Synthetic Procedures in Nucleic Acid Chemistry (Zorbach and Tipson, eds) 1: 189-193, "2'-Deoxyadenosine and 3'-Deoxyadenosine (Cordycepin)".

IPRP dated Jan. 19, 2010 in PCT/US2008/070383.

IPRP dated Oct. 26, 2012 in PCT/US2011/032143.

ISR and Written Opinion dated Aug. 26, 2011 in PCT/US2011/032143.

ISR and Written Opinion dated Dec. 17, 2008 in PCT/US2008/070383.

ISR and Written Opinion dated Feb. 23, 2015 in PCT/US2014/066328.

Ito et al. (2003) Nucleic Acids Research 31(10):2514-2523, "Synthesis, thermal stability and resistance to enzymatic hydrolysis of the oligonucleotides containing 5-(N-aminohexyl)carbamoyl-2'-O-methylurindines".

Kerr et al. (Feb. 9, 2000) Journal of Physical Chemistry B, 104(9):2166-2175, "Synthesis and Photophysics of a 1-Pyrenylmethyi-Substituted 2'-Deoxyuridine-5-Carboxamide Nucleoside:Electron-Transfer Product Lifetimes and Energies".

Latham et al. (1994)Nucleic Acids Research 22(14):2817-2822, "The application of a modified nucleotide in aptamer selection: novel thrombin aptamers containing 5-(1-pentynyl)-2'-deoxyuridine".

Mamas et al. (1992) Tetrahedron Letters 33(17): 2413-2416, "Straightforward C-8 alkylation of adenosine analogues with tetraalkyltin reagents".

Matsuda et al. (1979) Chemical and Pharmaceutical Bulletin, Pharmaceutical Society of Japan, Tokyo, JP 27(1): 183-192, "Nucleosides and nucleotides. XXVII. Synthesis of 2- and 8-cyanoadenosines and their derivatives".

Molecular Probes Handbook, 8th Edition, Section 8.2 (2001) "Labeling Oligonucleotides and Nucleic Acids".

Nomura et al. (1997) Nucleic Acids Research 25(14):2784-2791, "Site-specific introduction of functional groups into phosphodiester oligodeoxynucleotides and their thermal stability and nuclease-resistance properties".

Office Action dated Jun. 9, 2010 in U.S. Appl. No. 12/175,446.

Ono et al. (1994) Bioorg. & Med. Chem. Let. 4(2): 361-366, "Nucleosides and Nucleotides. 127. A novel and convenient post-synthetic modification method for the synthesis of oligodeoxyribonucleotides carrying amino linkers at the 5-position of 2'deoxyuridine".

(56) References Cited

OTHER PUBLICATIONS

Perlman et al. (1985) J. Med. Chem. 28(6): 741-748, "Nucleosides. 133. Synthesis of 5-alkenyl-1-(2-deoxy-2-fluoro-β-D-arabinofuranosyl) cytosines and related pyrimidine nucleosides as potential antiviral agents".

Ruth and Bergstrom (1978) J. Org. Chem. 43(14): 2870-2876, "C-5 substituted pyrimidine nucleosides. 1. Synthesis of C-5 allyl, propyl, and propenyl uracil and cytosine nucleosides via organopalladium intermediates".

Sagi et al. (1994) J. Med. Chem. 37: 1307-1311, "Synthesis and antiviral activities of 8-alkynyl-, 8-alkenyl-, and 8-alkyl-2'-deoxyadenosine analogues".

Saitoh et al. (2002) Nucleic Acids Research Supplement 2:215-216 "Modified DNA aptamers against sweet agent aspartame".

Seelig and Jaschke (1997) Tetrahedron Letters, 38(44):7729-7732, "Site-Specific Modification of Enzymatically Synthesized RNA: Transcription Initiation and Diels-Alder Reaction".

Silverman, R. B., "Bioisosterism," part of Chapter II of the Organic Chemistry of Drug Design and Drug Action, Academic Press, 1992, New York, NY, only pp. 4 and 19-23 supplied.

Tronchet et al. (1988) Nucleosides and Nucleotides, 7(2): 249-269, "3'-deoxy-3'-hydroxyamino-β-D-xylofuranosyluracil and derivatives thereof".

Ueno et al. (1997) Nucleic Acids Research 25(19):3777-3782, "Effects of 5-(N-aminohexyl)carbamoyl-2'-deoxyuridine on endonuclease stability and the ability of oligodeoxynucleotide to activate RNase H".

Uhlmann and Peyman (Jun. 1990) Chemical Reviews 90(4):544-584, "Antisense Oligonucleotides: A New Therapeutic Principle".

Van Aerschot et al. (1993) J. Med. Chem. 36: 2938-2942, "Antiviral activity of C-alkylated purine nucleosides obtained by cross-coupling with tetraalkyltin reagents".

Vaught et al. (Mar. 2010) J.Am. Chem. Soc. ePub, 132(12):4141-4151:4142, "Expanding the Chemistry of DNA for In Vitro Selection".

Vaught, Jonathan David, Thesis Oct. 2008 "Enhancing the Functionality of Nucleic Acids".

Tarasow et al. (Sep. 1997) Nature vol. 398:54-17, "RNA-catalysed carbon-carbon bond formation".

Tarasow et al. (1999) J. Am. Chem. Soc. 121:3614-3617, "Characteristics of a RNA-Diels-Alderase Active Site".

Tu et al. (1995) Nucleosides & Nucleotides 14(8):1631-1638, "Palladium Catalysts in the Synthesis of 8-Position Modified Adenosine, 2'-Deoxyadenosine and Guanosine".

Vaught et al. (2004) J. Am. Chem. Soc. 126:11231-11237, "T7 RNA Polymerase Transcription and 5-Position Modified UTP Derivatives".

Extended European Search Report dated Jul. 3, 2017 in EP 14864118.6.

Davies et al., "Unique motifs and hydrophobic interactions shape the binding of modified DNA ligands to protein targets", PNAS, vol. 109, No. 49, pp. 19971-19976, published on Dec. 4, 2012.

Lu et al. (Jun. 2013) Am Chem Soc, vol. 135, No. 25, pp. 9315-9317, "Chemical modification-assisted bisulfite sequencing (CAB-Seq) for 5-carboxylcytosine detection in DNA".

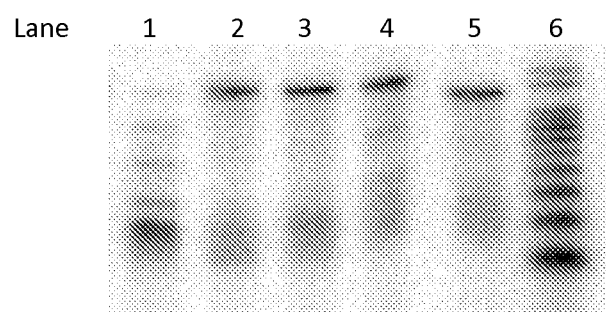

CYTIDINE-5-CARBOXAMIDE MODIFIED NUCLEOTIDE COMPOSITIONS AND METHODS RELATED THERETO

RELATED APPLICATIONS

This application is a 35 U.S.C. § 371 national phase application of International Application Serial No. PCT/US2014/066328 (WO 2015/077292), filed Nov. 19, 2014, International Application Serial No. PCT/US2014/006328 claims priority under 35 U.S.C. § 119(e) to U.S. provisional application Ser. No. 61/907,274, filed on Nov. 21, 2013, which is incorporated herein by reference in its entirety.

FIELD

The present disclosure relates generally to the field of nucleic acid chemistry, specifically to 5-position modified cytosine as well as phosphoramidites and triphosphates derivatives thereof. The present disclosure also relates to methods of making and using the same. The disclosure includes the use of the modified nucleosides as part of an oligonucleotide or an aptamer.

Incorporated by reference herein in its entirety is the Sequence Listing entitled "Sequences 0057.65PCT_ST25", created Oct. 2, 2014, size of 2 kilobytes.

BACKGROUND

Modified nucleosides have been used as therapeutic agents, diagnostic agents, and for incorporation into oligonucleotides to improve their properties (e.g., stability).

SELEX (Systematic Evolution of Ligands for EXponential Enrichment) is a method for identifying oligonucleotides (referred to as "aptamers") that selectively bind target molecules. The SELEX process is described in U.S. Pat. No. 5,270,163, the contents of which are herein incorporated by reference in their entirety. The SELEX method involves the selection and identification of oligonucleotides from a random mixture of oligonucleotides to achieve virtually any desired criterion of binding affinity and selectivity. By introducing specific types of modified nucleosides to the oligonucleotides identified in the course of the SELEX process, the nuclease stability, net charge, hydrophilicity or lipophilicity may be altered to provide differences in the three dimensional structure and target binding capabilities of the oligonucleotides. Thus, different modified nucleosides provide the ability to "tune" the desired properties of an oligonucleotide selected in the course of SELEX.

Modified deoxyuridine nucleotides, bearing an N-substituted-carboxamide group at the 5-position, have proven to be valuable tools for improving in vitro selection of protein-binding aptamers (SELEX process) (see, e.g., Gold et al., 2010; Hollenstein, 2012; and Imaizumi et al., 2013) and for post-SELEX optimization of binding and pharmacokinetic properties of the selected aptamers (see, e.g., Davies, et al., 2012; Lee et al., 2010; Kerr et al., 2000; and Gaballah et al., 2002). The general synthesis of uridine-5-carboxamides relied on a common activated ester intermediate, 5-(2,2,2-trifluoroethoxycarbonyl)-2'-deoxyuridine (1), which was originally reported by Matsuda and coworkers (see, e.g. Nomura et al., 1997). Treatment of this activated ester with various primary amines (1.2 eq., 60° C., 4 h) affords the corresponding 5-N-substituted-carboxamides). Matsuda also disclosed the analogous activated ester in the cytidine series, N-acetyl-5-(2,2,2-trifluoroethoxycarbonyl)-2'-deoxycytidine (see, e.g. Nomura et al., 1996). However, this intermediate was less practically useful for synthesis of cytidine-5-carboxamides due to the lability of the N-acetyl protecting group and the instability of the N-acetyl-5-iodo-cytidine synthetic precursors.

There continues to be a need for alternative composition for improving oligonucleotide target binding agents, and further methods for synthesizing such compositions. The present disclosure meets such needs by providing novel cytidine-5-carboxamide modified compositions.

SUMMARY

The present disclosure describes 5-position modified cytosine as well as phosphoramidites and triphosphates derivatives thereof, and to methods of making and using the same.

In one aspect, the disclosure provides for a compound comprising the structure shown in Formula I:

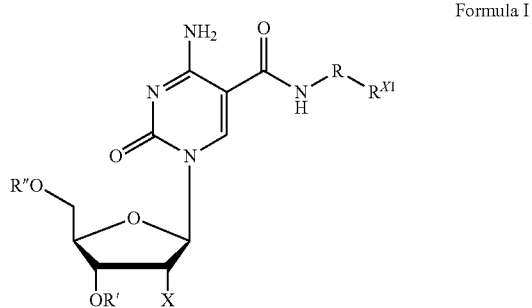

Formula I wherein

R is independently a —(CH$_2$)$_n$—, wherein n is an integer selected from 0, 1, 2, 3, 4, 5, 6, 7, 8, 9 or 10;

R$^{X1}$ is independently selected from the group consisting of:

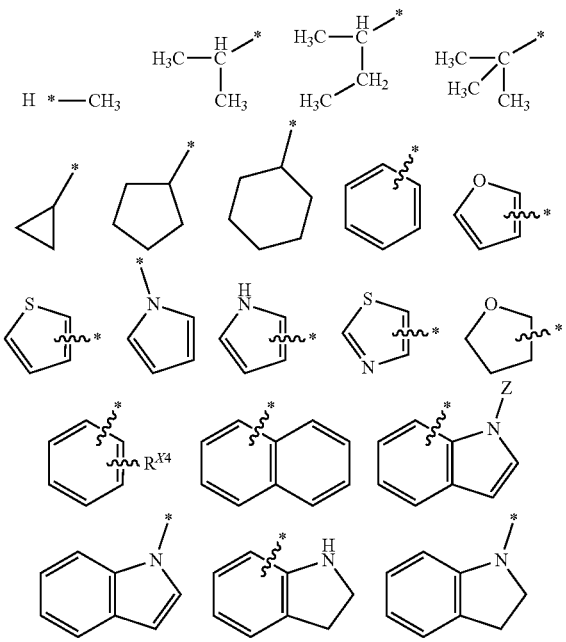

-continued

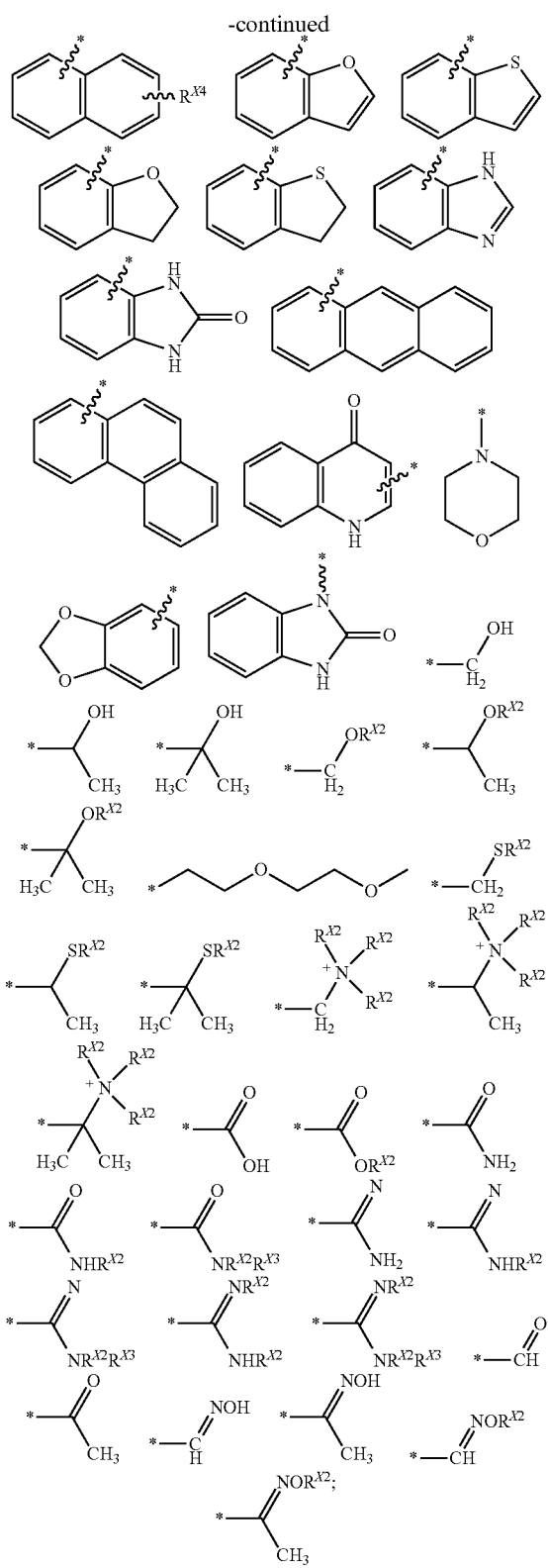

wherein * denotes the point of attachment of the $R^{X1}$ group to the —(CH$_2$)$_n$— group; and wherein $R^{X4}$ is independently selected from the group consisting of a substituted or unsubstituted branched or linear lower alkyl (C1-C20); a hydroxyl group; a halogen (F, Cl, Br, I); nitrile (CN); boronic acid (BO$_2$H$_2$); carboxylic acid (COOH); carboxylic acid ester (COOR$^{X2}$); primary amide (CONH$_2$); secondary amide (CONHR$^{X2}$); tertiary amide (CONR$^{X2}$R$^{X3}$); sulfonamide (SO$_2$NH$_2$); N-alkylsulfonamide (SONHR$^{X2}$);

$R^{X2}$ and $R^{X3}$ are independently, for each occurrence, selected from the group consisting of a substituted or unsubstituted branched or linear lower alkyl (C1-C20); phenyl (C$_6$H$_5$); an $R^{X4}$ substituted phenyl ring ($R^{X4}$C$_6$H$_4$), wherein $R^{X4}$ is defined above; a carboxylic acid (COOH); a carboxylic acid ester (COOR$^{X5}$), wherein $R^{X5}$ is a branched or linear lower alkyl (C1-C20); and cycloalkyl, wherein $R^{X2}$ and $R^{X3}$ together form a substituted or unsubstituted 5 or 6 membered ring;

X is independently selected from the group consisting of —H, —OH, —OMe, —O-allyl, —F, —OEt, —OPr, —OCH$_2$CH$_2$OCH$_3$, —NH$_2$ and -azido;

R' is independently selected from the group consisting of a —H, —OAc; —OBz; —P(NiPr$_2$)(OCH$_2$CH$_2$CN); and —OSiMe$_2$tBu;

R" is independently selected from the group consisting of a hydrogen, 4,4'-dimethoxytrityl (DMT) and triphosphate (—P(O)(OH)—O—P(O)(OH)—O—P(O)(OH)$_2$) or a salt thereof;

Z is independently selected from the group consisting of a —H, a substituted or unsubstituted branched or linear lower alkyl (C1-C4);

and salts thereof;

with the following exceptions:
when n=4, then $R^{X1}$ cannot be H;
when n=3, then $R^{X1}$ cannot be CH$_3$;
when n=0, then $R^{X1}$ cannot be —CH(CH$_3$)$_2$; and
when n=2, and $R^{X1}$ is

and $R^{X4}$ is hydroxyl then $R^{X1}$ cannot be

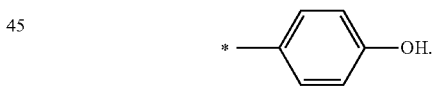

In related aspect n is an integer selected from 1, 2 or 3.
In related aspect, $R^{X1}$ is selected from the group consisting of:

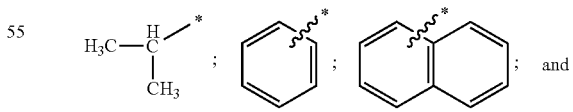

wherein
* denotes the point of attachment of the $R^{X1}$ group to the —(CH$_2$)$_n$— group; and Z is independently selected from the group consisting of a —H, a substituted or unsubstituted branched or linear lower alkyl (C1-C4).

In related aspect, $R^{x4}$ is independently selected from the group consisting of a branched or linear lower alkyl (C1-C6); —OH; —F and carboxylic acid (COOH).

In related aspect, X is independently selected from the group consisting of —H, —OH, —OMe and —F.

In related aspect, R' is selected from the group consisting of a —H, —OAc and —P(NiPr$_2$)(OCH$_2$CH$_2$CN).

In related aspect, R" is a triphosphate (—P(O)(OH)—O—P(O)(OH)—O—P(O)(OH)$_2$).

In another aspect, the disclosure provides for a compound comprising the structure selected from the group consisting of Formulas II (BndC), III (PEdC), IV (PPdC), V (NapdC), VI (2NapdC), VII (NEdC) and VIII (2NEdC):

Formula II
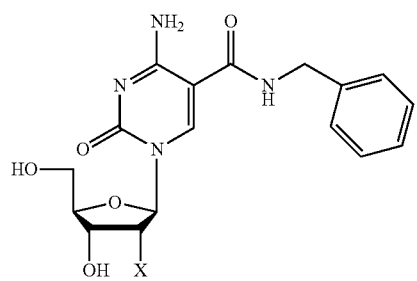
;

Formula III
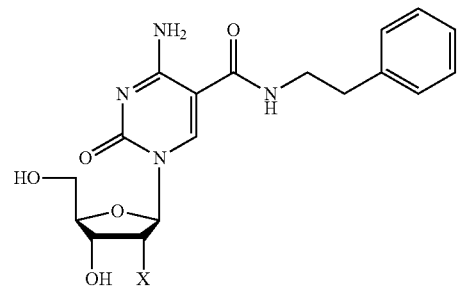
;

Formula IV
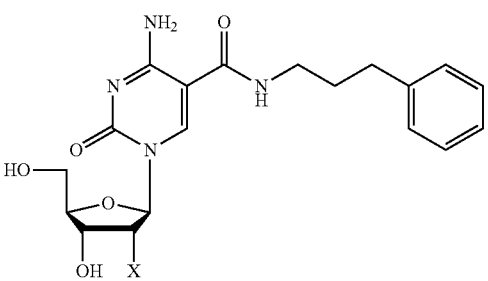
;

Formula V
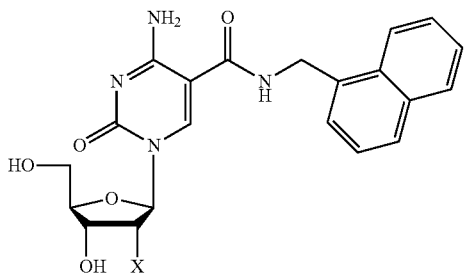
;

Formula VI
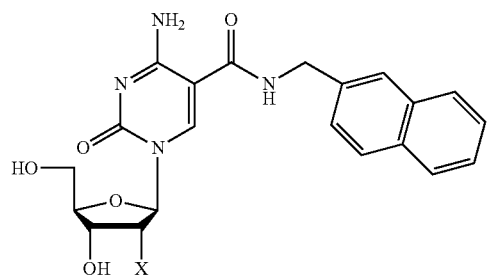
;

Formula VII
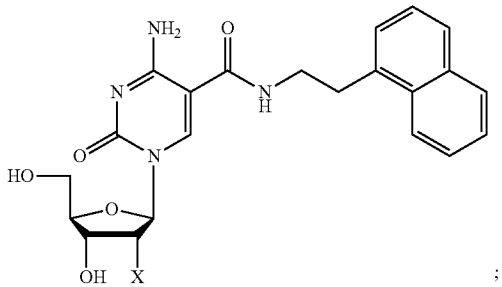
; or

Formula VIII
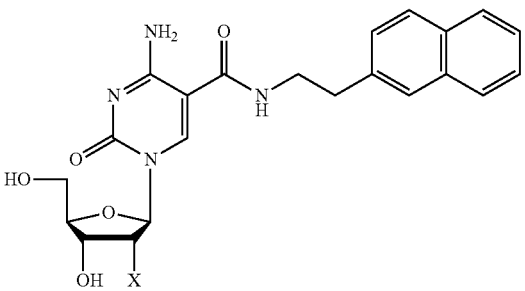
;

wherein

X is independently selected from the group consisting of —H, —OH, —OMe, —O-allyl, —F, —OEt, —OPr, —OCH$_2$CH$_2$OCH$_3$, —NH$_2$ and -azido.

In another aspect, the disclosure provides for a nucleic acid molecule comprising any one of the compounds described above.

In a related aspect, the nucleic acid molecule comprises RNA, DNA or a combination thereof.

In a related aspect, the nucleic acid molecule is from 15 to 100 nucleotides in length.

In a related aspect, the nucleic acid molecule is an aptamer.

In a related aspect, at least one additional nucleotide of the nucleic acid molecule comprises a chemical modification selected from the group consisting of a 2'-position sugar modification including but not limited to, a 2'-amino (2'-NH$_2$), 2'-fluoro (2'-F), 2'-O-methyl (2'-OMe), 2'-O-ethyl (2'-OEt), 2'-O-propyl (2'-OPr), 2'-O—CH$_2$CH$_2$OCH$_3$ and azido.

In another aspect, the disclosure provides for a nucleic acid molecule comprising a compound comprising the structure shown in Formula IA:

Formula IA

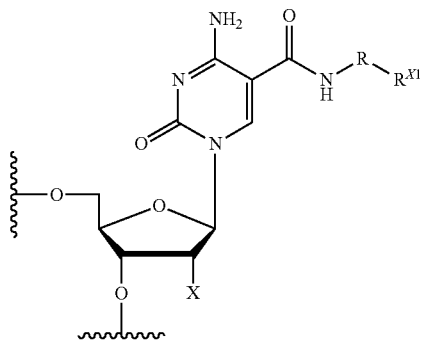

wherein

R is independently a —(CH$_2$)$_n$—, wherein n is an integer selected from 0, 1, 2, 3, 4, 5, 6, 7, 8, 9 or 10;

R$^{X1}$ is independently selected from the group consisting of:

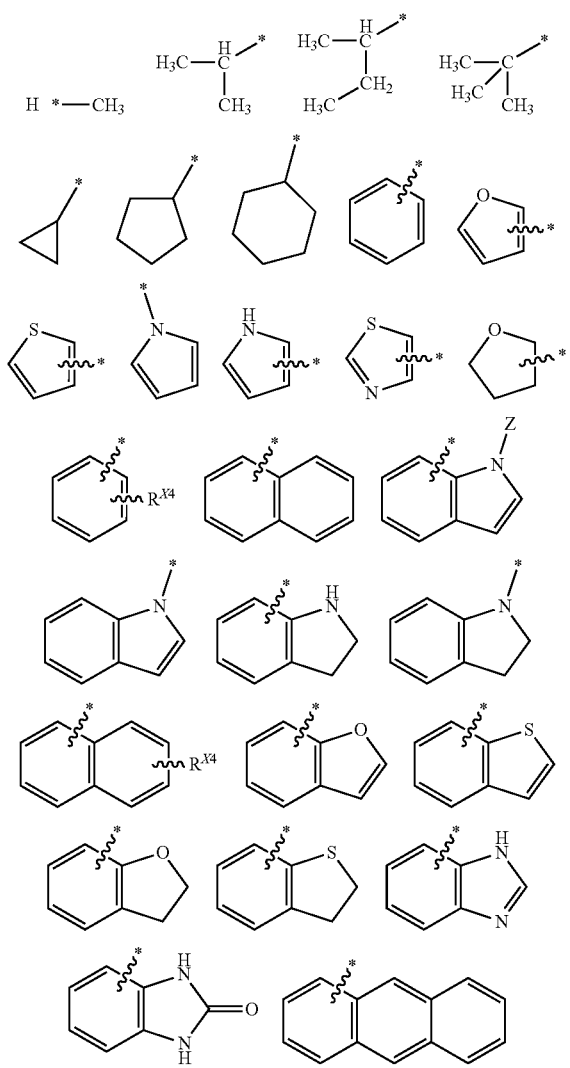

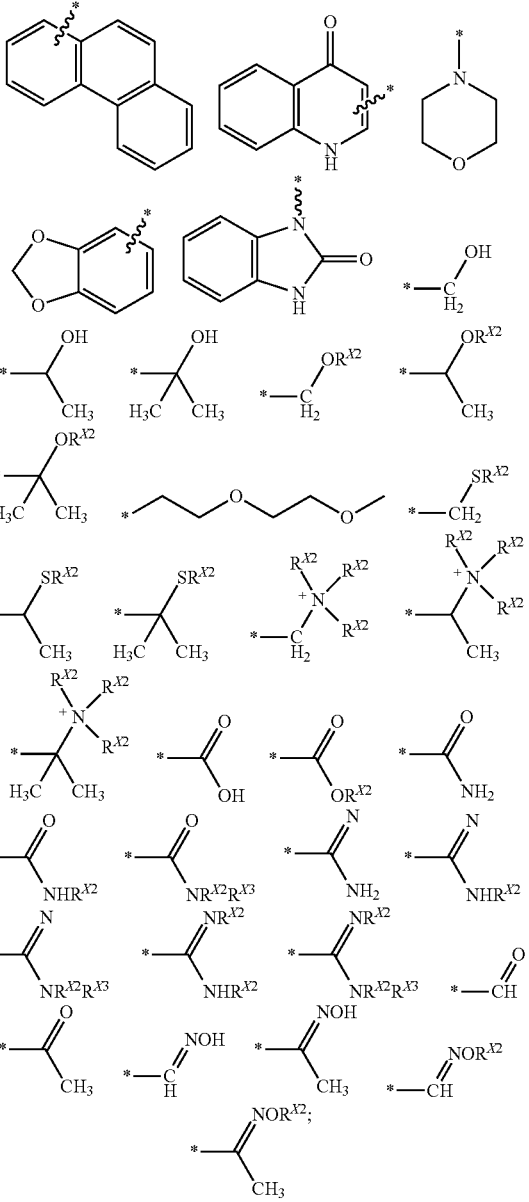

wherein, * denotes the point of attachment of the R$^{X1}$ group to the —(CH$_2$)$_n$— group; and wherein, R$^{X4}$ is independently selected from the group consisting of a branched or linear lower alkyl (C1-C20); a hydroxyl group; halogen (F, Cl, Br, I); nitrile (CN); boronic acid (BO$_2$H$_2$); carboxylic acid (COOH); carboxylic acid ester (COOR$^{X2}$); primary amide (CONH$_2$); secondary amide (CONHR$^{X2}$); tertiary amide (CONR$^{X2}$R$^{X3}$); sulfonamide (SO$_2$NH$_2$); N-alkylsulfonamide (SONHR$^{X2}$);

R$^{X2}$ and R$^{X3}$ are independently, for each occurrence, selected from the group consisting of a branched or linear lower alkyl (C1-C20); phenyl (C$_6$H$_5$); an R$^{X4}$ substituted phenyl ring (R$^{X4}$C$_6$H$_4$), wherein R$^{X4}$ is defined above; a carboxylic acid (COOH); a carboxylic acid ester (COOR$^{X5}$), wherein R$^{X5}$ is a branched or linear lower alkyl (C1-C20); and cycloalkyl, wherein R$^{X2}$ and R$^{X3}$ together form a substituted or unsubstituted 5 or 6 membered ring;

X is independently selected from the group consisting of —H, —OH, —OMe, —O-allyl, —F, —OEt, —OPr, —OCH$_2$CH$_2$OCH$_3$, NH$_2$ and -azido;

Z is independently selected from the group consisting of a —H, a substituted or unsubstituted C(1-4)alkyl; and salts thereof;
with the following exceptions:
when n=4, then $R^{X1}$ cannot be H;
when n=3, then $R^{X1}$ cannot be $CH_3$;
when n=0, then $R^{X1}$ cannot be —$CH(CH_3)_2$; and
when n=2, and $R^{X1}$ is

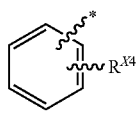

and $R^{X4}$ is hydroxyl then $R^{X1}$ cannot be

In a related aspect, n is 1, 2 or 3.
In a related aspect, $R^{X1}$ is selected from the group consisting of:

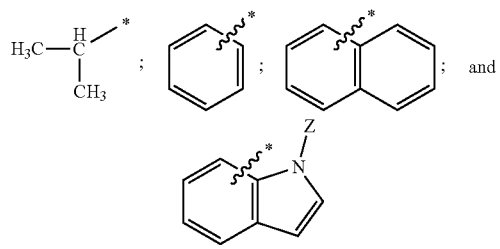

wherein,
* denotes the point of attachment of the $R^{X1}$ group to the —$(CH_2)_n$— group; and
Z is independently selected from the group consisting of a —H, a substituted or unsubstituted C(1-4)alkyl.
In a related aspect, $R^{X4}$ is independently selected from the group consisting of a branched or linear lower alkyl (C1-C6); a —OH; a —F and carboxylic acid (COOH).
In a related aspect, X is independently selected from the group consisting of —H, —OH, —OMe and —F.
In a related aspect, R' is selected from the group consisting of a —H, —OAc and —P(NiPr$_2$)(OCH$_2$CH$_2$CN).
In a related aspect, R" is a triphosphate (—P(O)(OH)—O—P(O)(OH)—O—P(O)(OH)$_2$).
In a related aspect, the nucleic acid molecule comprises DNA, RNA or a combination thereof.
In a related aspect, the nucleic acid molecule is from 15 to 100 nucleotides in length.
In a related aspect, the nucleic acid molecule is an aptamer.
In a related aspect, at least one additional nucleotide of the nucleic acid molecule comprises a chemical modification selected from the group consisting of a 2'-position sugar modification independently selected from the group consisting of 2'-amino (2'-NH$_2$), 2'-fluoro (2'-F), 2'-O-methyl (2'-OMe), 2'-O-ethyl (2'-OEt), 2'-O-propyl (2'-OPr), 2'-O—CH$_2$CH$_2$OCH$_3$ and azido.

In a related aspect, the nucleic acid molecule further comprises a modification selected from the group consisting of a backbone modification, a 3' cap, a 5' cap and a combination thereof.

In a related aspect, the compound comprises the structure selected from the group consisting of Formulas IIA, IIIA, IVA, VA, VIA, VIIA and VIIIA:

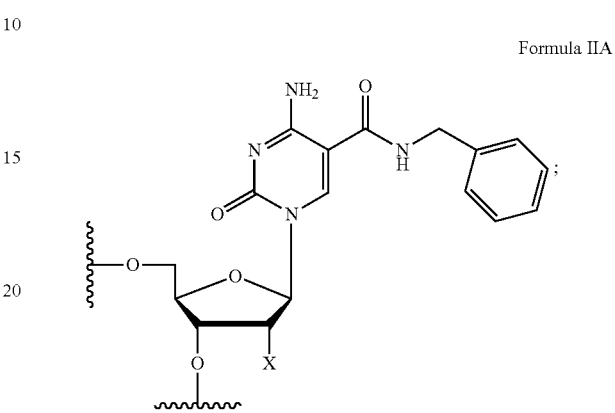

Formula IIA

Formula IIIA

Formula IVA

-continued

Formula VA

Formula VIA

Formula VIIA

Formula VIIIA wherein
X is independently selected from the group consisting of —H, —OH, —OMe, —O-allyl, —F, —OEt, —OPr, —OCH₂CH₂OCH₃, NH₂ and -azido.

In another aspect, the disclosure provides for a method for making a compound having Formula I:

Formula I wherein
R is independently a —(CH₂)$_n$—, wherein n is an integer selected from 0, 1, 2, 3, 4, 5, 6, 7, 8, 9 or 10;
$R^{X1}$ is independently selected from the group consisting of:

-continued

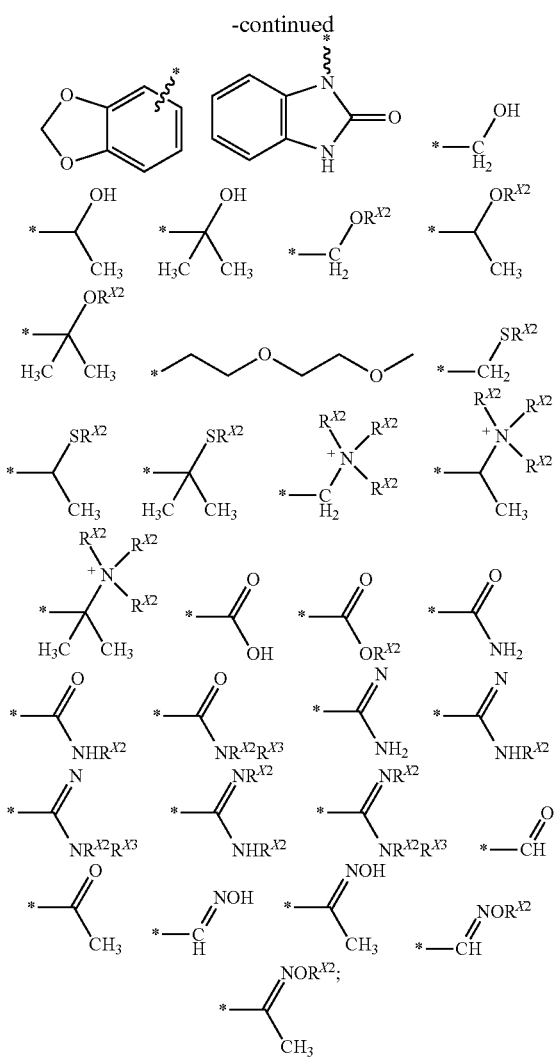

wherein, * denotes the point of attachment of the $R^{X1}$ group to the —$(CH_2)_n$— group; and wherein, $R^{X4}$ is independently selected from the group consisting of a branched or linear lower alkyl (C1-C20); a hydroxyl group; halogen (F, Cl, Br, I); nitrile (CN); boronic acid ($BO_2H_2$); carboxylic acid (COOH); carboxylic acid ester ($COOR^{X2}$); primary amide ($CONH_2$); secondary amide ($CONHR^{X2}$); tertiary amide ($CONR^{X2}R^{X3}$); sulfonamide ($SO_2NH_2$); N-alkylsulfonamide ($SONHR^{X2}$);

$R^{X2}$ and $R^{X3}$ are independently, for each occurrence, selected from the group consisting of a branched or linear lower alkyl (C1-C20); phenyl ($C_6H_5$); an $R^{X4}$ substituted phenyl ring ($R^{X4}C_6H_4$), wherein $R^{X4}$ is defined above; a carboxylic acid (COOH); a carboxylic acid ester ($COOR^{X5}$), wherein $R^{X5}$ is a branched or linear lower alkyl (C1-C20); and cycloalkyl, wherein $R^{X2}$ and $R^{X3}$ together form a substituted or unsubstituted 5 or 6 membered ring;

X is independently selected from the group consisting of —H, —OH, —OMe, —O-allyl, —F, —OEt, —OPr, —$OCH_2CH_2OCH_3$, $NH_2$ and -azido;

Z is independently selected from the group consisting of a —H, a substituted or unsubstituted C(1-4)alkyl;

the method comprising providing a compound having Formula IX

Formula IX

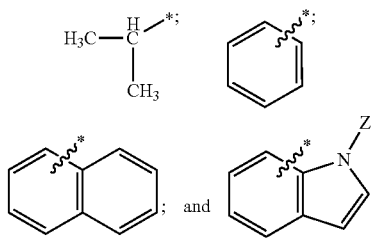

wherein,
$R^{X6}$ is an iodine or bromine group;
$R^{X7}$ and $R^{X8}$ are independently, for each occurrence, a hydrogen or a protecting group;
X is independently selected from the group consisting of —H, —OH, —OMe, —O-allyl, —F, —OEt, —OPr, —$OCH_2CH_2OCH_3$, $NH_2$ and -azido; and
transforming the compound having Formula IX by a palladium(0) catalyzed reaction in the presence of $R^{X1}$— R—$NH_2$, carbon monoxide and a solvent; and
isolating the compound having Formula I.
In a related aspect, $R^{X6}$ is an iodine group.
In a related aspect, $R^{X7}$ and $R^{X8}$ are a hydrogen.
In a related aspect, X is selected from the group consisting of a —H, —OMe and —F.
In a related aspect, n is 1, 2 or 3.
In a related aspect, $R^{X1}$ is selected from the group consisting of:

wherein,
* denotes the point of attachment of the $R^{X1}$ group to the —$(CH_2)_n$— group; and
Z is independently selected from the group consisting of a —H, a substituted or unsubstituted C(1-4)alkyl.
In a related aspect, $R^{X4}$ is independently selected from the group consisting of a branched or linear lower alkyl (C1-C6); a —OH; a —F and carboxylic acid (COOH).
In a related aspect, R' is selected from the group consisting of a —H, —OAc and —$P(NiPr_2)(OCH_2CH_2CN)$.
In a related aspect, R" is a hydrogen or triphosphate (—P(O)(OH)—O—P(O)(OH)—O—P(O)(OH)$_2$).
In a related aspect, the protecting group is selected from the group consisting of triphenylmethyl, p-anisyldiphenylmethyl, di-p-anisyldiphenylmethyl, p-dimethoxy trityltrityl, formyl, t-butyloxycarbonyl, benzyloxycarbonyl, 2-chlorobenzyloxycarbonyl, 4-chlorobenzoyloxycarbonyl, 2,4-dichlorobenzyloxycarbonyl, furfurylcarbonyl, t-amyloxycarbonyl, adamantyloxycarbonyl, 2-phenylpropyl-(2)-oxycarbonyl, 2-(4-biphenyl)propyl-(2)-oxycarbonyl, 2-nitrophenylsulfenyl and diphenylphosphinyl.

In a related aspect, the solvent is selected from the group consisting of dimethylformamide (DMF), dichloromethane (DCM), tetrahydrofuran (THF), ethyl acetate, acetone, acetonitrile (MeCN), dimethyl sulfoxide (DMSO) and propylene carbonate.

In another aspect, the disclosure provides for a method for making a compound having a formula selected from the group consisting of Formulas II, III, IV, V, VI, VII and VIII Formula II
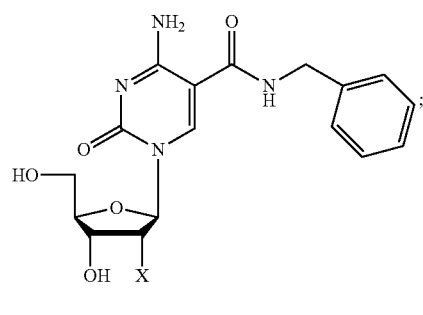

Formula III
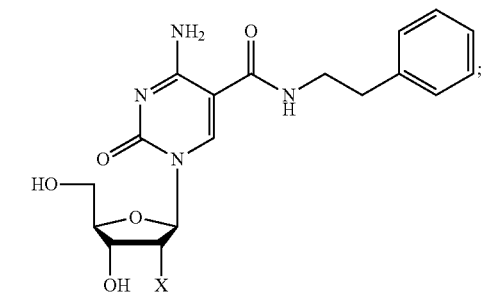

Formula IV
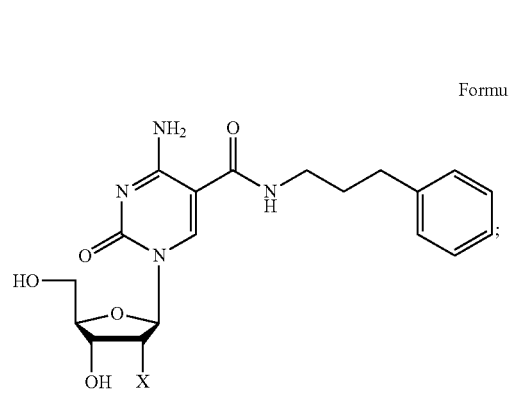

Formula V
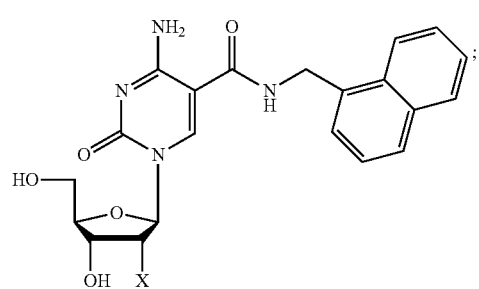

Formula VI
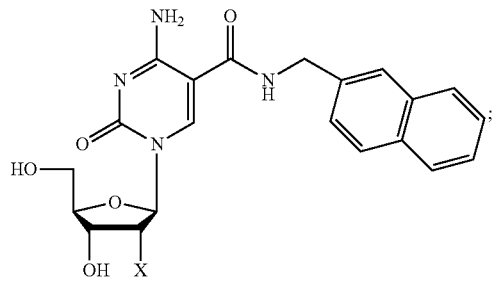

Formula VII
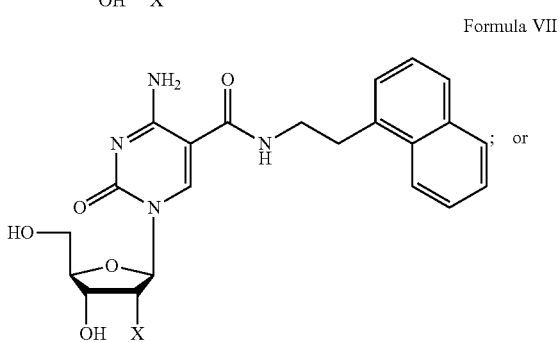

Formula VIII
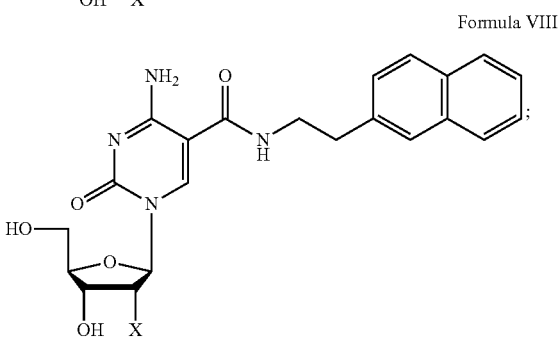

wherein
X is independently selected from the group consisting of —H, —OH, —OMe, —O-allyl, —F, —OEt, —OPr, —OCH$_2$CH$_2$OCH$_3$, NH$_2$ and -azido;
the method comprising providing a compound having Formula IX Formula IX
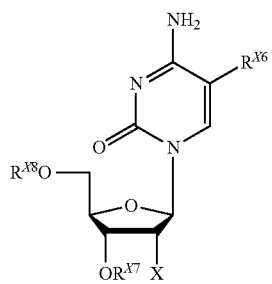

wherein,
R$^{X6}$ is an iodine or bromine group;
R$^{X7}$ and R$^{X8}$ independently, independently, for each occurrence, a hydrogen or protecting group;
X is independently selected from the group consisting of —H, —OH, —OMe, —O-allyl, —F, —OEt, —OPr, —OCH$_2$CH$_2$OCH$_3$ and -azido; and transforming the compound having Formula IX by a palladium(0) catalyzed reaction in the presence of $R^{X1}$—R—$NH_2$, carbon monoxide and a solvent; and isolating the compound having the formula selected from the group consisting of Formulas II, III and IV.

In a related aspect, $R^{X6}$ is an iodine group.

In a related aspect, $R^{X7}$ and $R^{X8}$ are hydrogen.

In a related aspect, X is selected from the group consisting of a —H, —OMe and —F.

In a related aspect, the protecting group is selected from the group consisting of triphenylmethyl, p-anisyldiphenylmethyl, di-p-anisyldiphenylmethyl, p-dimethoxy trityltrityl, formyl, t-butyloxycarbonyl, benzyloxycarbonyl, 2-chlorobenzyloxycarbonyl, 4-chlorobenzoyloxycarbonyl, 2,4-dichlorobenzyloxycarbonyl, furfurylcarbonyl, t-amyloxycarbonyl, adamantyloxycarbonyl, 2-phenylpropyl-(2)-oxycarbonyl, 2-(4-biphenyl)propyl-(2)-oxycarbonyl, 2-nitrophenylsulfenyl and diphenylphosphinyl.

In a related aspect, the solvent is selected from the group consisting of dimethylformamide (DMF), dichloromethane (DCM), tetrahydrofuran (THF), ethyl acetate, acetone, acetronitrile (MeCN), dimethyl sulfoxide (DMSO) and propylene carbonate.

The present disclosure further provide for a method for selecting a nucleic acid aptamer having binding affinity for a target molecule comprising: (a) contacting a candidate mixture with the target, wherein the candidate mixture comprises modified nucleic aptamers in which one, several or all pyrimidines in at least one, or each, nucleic acid aptamer of the candidate mixture comprises a compound described herein (5-position modified cytosine), and wherein nucleic acid aptamers having binding affinity for the target molecule form nucleic acid aptamer-target molecule complexes; (b) partitioning the nucleic acid aptamer-target molecule complexes from the candidate mixture; (c) dissociating the nucleic acid aptamer-target molecule complexes to generate free nucleic acid aptamers; (d) amplifying the free nucleic acid aptamers to yield nucleic acid aptamers having an increased dissociation half-life from the target molecule relative to other nucleic acids in the candidate mixture; (e) identifying at least one nucleic acid aptamer, wherein the nucleic acid aptamer has binding affinity for the target molecule.

In another aspect, steps a) through d) are repeated with the mixture of nucleic acid aptamers enriched in nucleic acid sequences capable of binding to the target molecule and have a slow off-rate when bound to the target molecule to further enrich for nucleic acid sequences that are capable of binding to the target molecule and have a slow off-rate when bound to the target molecule.

In another aspect, the rate of dissociation of the slow off-rate nucleic acid aptamer is from about 2 minutes to about 360 minutes (or from about 2, 3, 4, 5, 6, 7, 8, 9, 10, 15, 20, 25, 30, 45, 60, 75, 90, 105, 120, 150, 180, 210, 240, 270, 300, 330 or 360 minutes).

In another aspect the rate of dissociation of the slow off-rate nucleic acid aptamer is greater than or equal to about 2 minutes (or greater than about 2, 3, 4, 5, 6, 7, 8, 9, 10, 15, 20, 25, 30, 45, 60, 75, 90, 105, 120, 150, 180, 210, 240, 270, 300, 330 or 360 minutes).

In another aspect the target molecule is a protein or a peptide.

In another aspect the target molecule is selected from the group consisting of a PSCK9 protein, a PSMA protein, ERBB2 protein and a ERBB3 protein.

In another aspect the at least one nucleic acid aptamer is capable of binding the target molecule with an equilibrium binding constant ($K_d$) of at less than 100 nM, or from about 0.1 nM to about 100 nM (or from 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 90, 91, 92, 93, 94, 95, 96, 97, 98, 99 or 100 nM).

In another aspect, the methods described herein further comprise exposing the candidate mixture to a slow off-rate enrichment process.

In another aspect, the slow off-rate enrichment process is performed prior to step (b). In a related aspect, the slow off-rate enrichment process is selected from the group consisting of adding a competitor molecule, a dilution step, a combination of adding a competitor molecule followed by a dilution step, a combination of a dilution step followed by a adding a competitor molecule, and a combination of simultaneously adding a competitor molecule and a dilution step.

In yet another related aspect, the competitor molecule is a polyanion. In another aspect, the competitor molecule is selected from the group consisting of an oligonucleotide, dNTPs, heparin and dextran sulfate.

The foregoing and other objects, features, and advantages of the invention will become more apparent from the following detailed description, which proceeds with reference to the accompanying FIGURES.

BRIEF DESCRIPTION OF THE DRAWINGS

FIG. 1 shows a polyacrylamide gel image of a primer extension assay with DNTP's as described in the Materials and Methods section of the Examples. Lane 1: dAdGdT (5% full length); Lane 2: dAdGdTdC (100% full length); Lane 3: dAdGdT+9a (119% full length); Lane 4: dAdGdT+9b (113% full length); Lane 5: dAdGdT+9c (120% full length); Lane 6: 20/200 DNA Ladder. With reference to this FIGURE it can be seen that all three modified cytidine triphosphates were incorporated at least as efficiently as natural, unmodified 2'-deoxycytidine in this assay.

DETAILED DESCRIPTION

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms wherein, * denotes the point of attachment of the $R^{X1}$ group to the —$(CH_2)_n$— group; and wherein, * denotes the point of attachment of the $R^{X1}$ group to the —$(CH_2)_n$— group; and "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Further, ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). Any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" mean±20% of the indicated range, value, or structure, unless otherwise indicated. As used herein, the terms "include" and "comprise" are open ended and are used synonymously. It should be understood that the terms "a" and "an" as used herein refer to "one or more" of the enumerated components. The use of the alternative (e.g., "or") should be understood to mean either one, both, or any combination thereof of the alternatives Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

As used herein, the term "nucleotide" refers to a ribonucleotide or a deoxyribonucleotide, or a modified form thereof, as well as an analog thereof. Nucleotides include species that include purines (e.g., adenine, hypoxanthine, guanine, and their derivatives and analogs) as well as pyrimidines (e.g., cytosine, uracil, thymine, and their derivatives and analogs).

As used herein, the term "C-5 modified carboxamidecytidine" or "cytidine-5-carboxamide" refers to a cytidine with a carboxyamide (—C(O)NH—) modification at the C-5 position of the cytidine including, but not limited to, those moieties ($R^{X1}$) illustrated herein. Example C-5 modified carboxamidecytidine include, but are not limited to, 5-(N-benzylcarboxamide)-2'-deoxycytidine (referred to as "BndC" and shown below as Formula (II); 5-(N-2-phenylethylcarboxamide)-2'-deoxycytidine (referred to as "PEdC" and shown below as Formula (III); 5-(N-3-phenylpropylcarboxamide)-2'-deoxycytidine (referred to as "PPdC" and shown below as Formula (IV); 5-(N-1-naphthylmethylcarboxamide)-2'-deoxycytidine (referred to as "NapdC" and shown below as Formula (V); 5-(N-2-naphthylmethylcarboxamide)-2'-deoxycytidine (referred to as "2NapdC" and shown below as Formula (VI); 5-(N-1-naphthyl-2-ethylcarboxamide)-2'-deoxycytidine (referred to as "NEdC" and shown below as Formula (VII); and 5-(N-2-naphthyl-2-ethylcarboxamide)-2'-deoxycytidine (referred to as "2NEdC" and shown below as Formula (VIII):

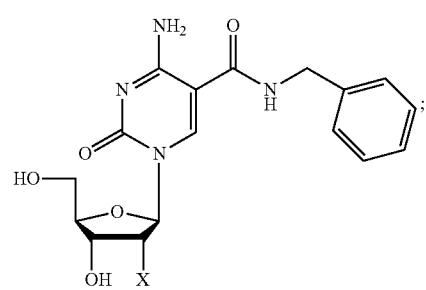

Formula II

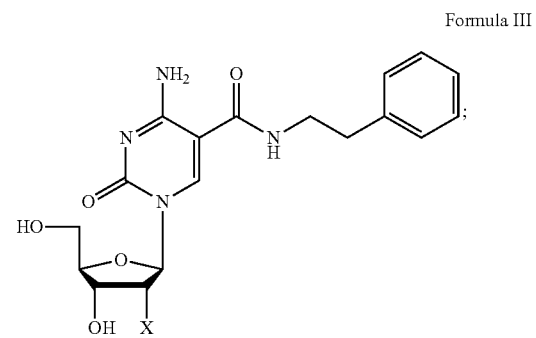

Formula III

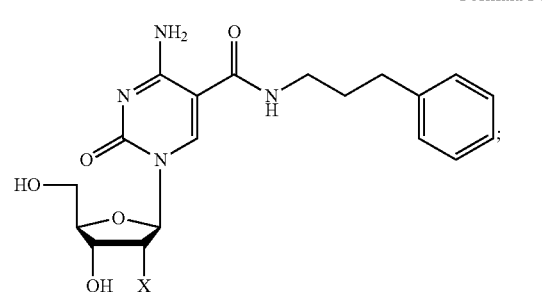

Formula IV

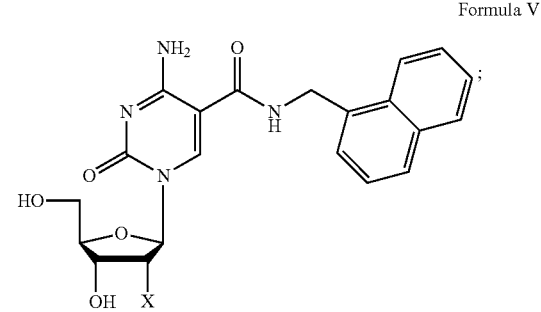

Formula V

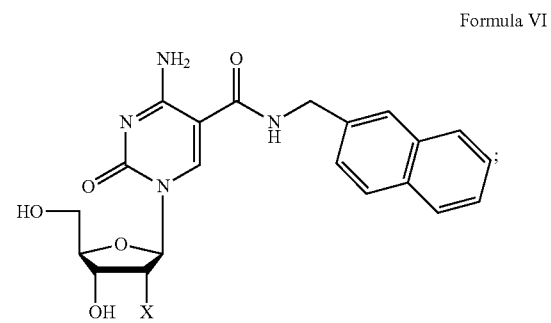

Formula VI

Formula VII

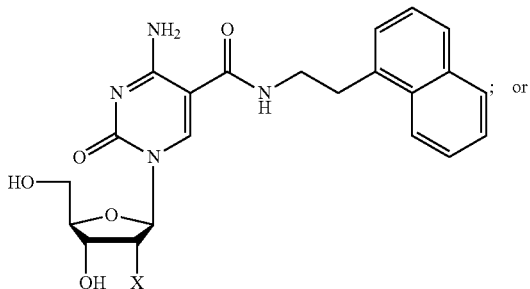

or

Formula VIII

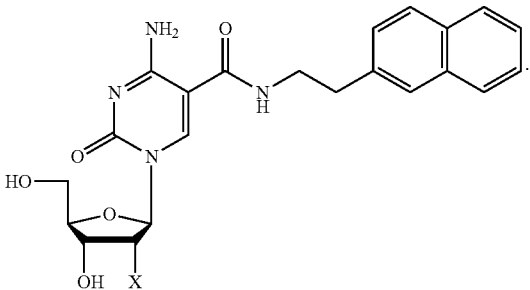

Chemical modifications of the C-5 modified cytidines described herein can also be combined with, singly or in any combination, 2'-position sugar modifications, modifications at exocyclic amines, and substitution of 4-thiocytidine and the like.

Salts

It may be convenient or desirable to prepare, purify, and/or handle a corresponding salt of the compound, for example, a pharmaceutically-acceptable salt. Examples of pharmaceutically acceptable salts are discussed in Berge et al. (1977) "Pharmaceutically Acceptable Salts" J. Pharm. Sci. 66:1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^{X+}$, $NH_2R^X_2{}^+$, $NHR^X_3{}^+$, $NR^X_4{}^+$). Examples of some suitable substituted ammonium ions are those derived from: ethylamine, diethylamine, dicyclohexylamine, triethylamine, butylamine, ethylenediamine, ethanolamine, diethanolamine, piperizine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Preparation of Oligonucleotides

In one aspect, the instant disclosure provides methods for using the modified nucleosides described herein, either alone or in combination with other modified nucleosides and/or naturally occurring nucleosides, to prepare modified oligonucleotides. The automated synthesis of oligodeoxynucleosides is routine practice in many laboratories (see e.g., Matteucci, M. D. and Caruthers, M. H., (1990) J. Am. Chem. Soc., 103:3185-3191, the contents of which are hereby incorporated by reference in their entirety). Synthesis of oligoribonucleosides is also well known (see e.g. Scaringe, S. A., et al., (1990) Nucleic Acids Res. 18:5433-5441, the contents of which are hereby incorporated by reference in their entirety). As noted herein, the phosphoramidites are useful for incorporation of the modified nucleoside into an oligonucleotide by chemical synthesis, and the triphosphates are useful for incorporation of the modified nucleoside into an oligonucleotide by enzymatic synthesis. (See e.g., Vaught, J. D. et al. (2004) J. Am. Chem. Soc., 126:11231-11237; Vaught, J. V., et al. (2010) J. Am. Chem. Soc. 132, 4141-4151; Gait, M. J. "Oligonucleotide Synthesis a practical approach" (1984) IRL Press (Oxford, UK); Herdewijn, P. "Oligonucleotide Synthesis" (2005) (Humana Press, Totowa, N.J. (each of which is incorporated herein by reference in its entirety).

As used herein, the terms "modify," "modified," "modification," and any variations thereof, when used in reference to an oligonucleotide, means that at least one of the four constituent nucleotide bases (i.e., A, G, T/U, and C) of the oligonucleotide is an analog or ester of a naturally occurring nucleotide. In some embodiments, the modified nucleotide confers nuclease resistance to the oligonucleotide. Additional modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in one embodiment ranging from about 10 to about 80 kDa, PEG polymers in another embodiment ranging from about 20 to about 60 kDa, or other hydrophilic or hydrophobic biological or synthetic polymers.

Polynucleotides can also contain analogous forms of ribose or deoxyribose sugars that are generally known in the art, including 2'-O-methyl, 2'-O-allyl, 2'-O-ethyl, 2'-O-propyl, 2'-O—$CH_2CH_2OCH_3$, 2'-fluoro, 2'-$NH_2$ or 2'-azido, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted herein, one or more phosphodiester linkages may be replaced by alternative linking groups. These alternative linking groups include embodiments wherein phosphate is replaced by P(O)S ("thioate"), P(S)S ("dithioate"), (O)$NR^X_2$ ("amidate"), P(O) $R^X$, P(O)$OR^{X'}$, CO or $CH_2$ ("formacetal"), in which each $R^X$ or $R^{X'}$ are independently H or substituted or unsubstituted alkyl (C1-C20) optionally containing an ether (—O—) linkage, aryl, alkenyl, cycloalky, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

Polynucleotides can also contain analogous forms of carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside.

If present, a modification to the nucleotide structure can be imparted before or after assembly of a polymer. A sequence of nucleotides can be interrupted by non-nucleotide components. A polynucleotide can be further modified after polymerization, such as by conjugation with a labeling component.

As used herein, "nucleic acid," "oligonucleotide," and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included. The terms "polynucleotide," "oligonucleotide," and "nucleic acid" include double- or single-stranded molecules as well as triple-helical molecules. Nucleic acid, oligonucleotide, and polynucleotide are broader terms than the term aptamer and, thus, the terms nucleic acid, oligonucleotide, and polynucleotide include polymers of nucleotides that are aptamers but the terms nucleic acid, oligonucleotide, and polynucleotide are not limited to aptamers.

In certain embodiments, the disclosure provides for a method for making a nucleic acid molecule comprising a compound having Formula I:

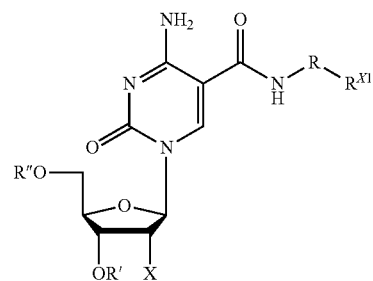

Formula I wherein

R is independently a —$(CH_2)_n$—, wherein n is an integer selected from 0, 1, 2, 3, 4, 5, 6, 7, 8, 9 or 10;

$R^{X1}$ is independently selected from the group consisting of

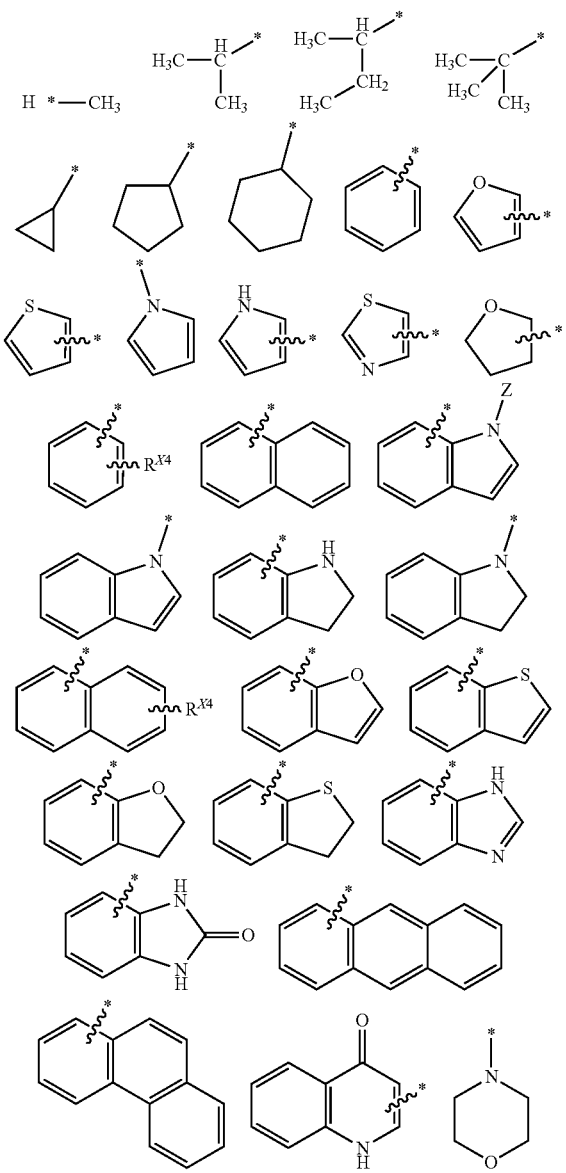

-continued

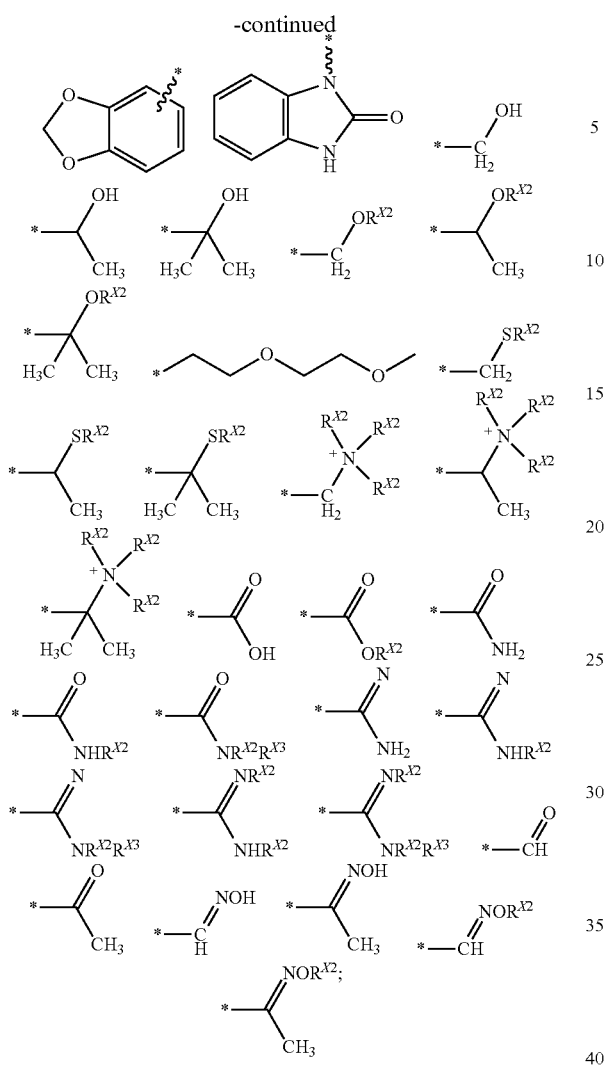

wherein, * denotes the point of attachment of the $R^{X1}$ group to the —$(CH_2)_n$— group; and wherein, $R^{X4}$ is independently selected from the group consisting of a branched or linear lower alkyl (C1-C20); a hydroxyl group; a halogen (F, Cl, Br, I); nitrile (CN); boronic acid ($BO_2H_2$); carboxylic acid (COOH); carboxylic acid ester ($COOR^{X2}$); primary amide ($CONH_2$); secondary amide ($CONHR^{X2}$); tertiary amide ($CONR^{X2}R^{X3}$); sulfonamide ($SO_2NH_2$); N-alkylsulfonamide ($SONHR^{X2}$);

$R^{X2}$ and $R^{X3}$ are independently, for each occurrence, selected from the group consisting of a branched or linear lower alkyl (C1-C20); phenyl ($C_6H_5$); an $R^{X4}$ substituted phenyl ring ($R^{X4}C_6H_4$), wherein $R^{X4}$ is defined above; a carboxylic acid (COOH); a carboxylic acid ester ($COOR^{X5}$), wherein $R^{X5}$ is a branched or linear lower alkyl (C1-C20); and cycloalkyl, wherein $R^{X2}$ and $R^{X3}$ together form a substituted or unsubstituted 5 or 6 membered ring;

X is independently selected from the group consisting of —H, —OH, —OMe, —O-allyl, —F, —OEt, —OPr, —$OCH_2CH_2OCH_3$, $NH_2$ and -azido;

R' is independently selected from the group consisting of a —H, —OAc; —OBz; —$P(NiPr_2)(OCH_2CH_2CN)$; and —$OSiMe_2tBu$;

R" is independently selected from the group consisting of a hydrogen, 4,4'-dimethoxytrityl (DMT) and triphosphate (—P(O)(OH)—O—P(O)(OH)—O—P(O)(OH)$_2$) or a salt thereof;

Z is independently selected from the group consisting of a —H, a substituted or unsubstituted C(1-4)alkyl;

and salts thereof, the method comprising synthesizing a nucleic acid molecule having a plurality of nucleotides and at least one compound having Formula I.

In certain embodiments, the disclosure provides for method for making a nucleic acid molecule comprising a compound having a formula selected from the group consisting of Formulas II, III, IV, V, VI, VII and VIII:

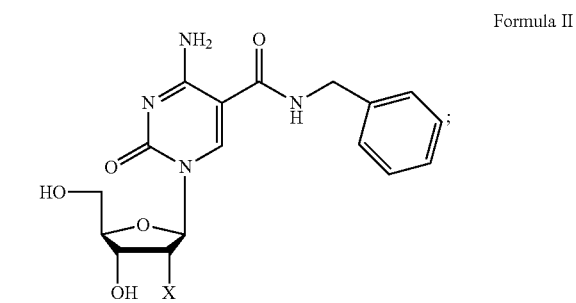

Formula II

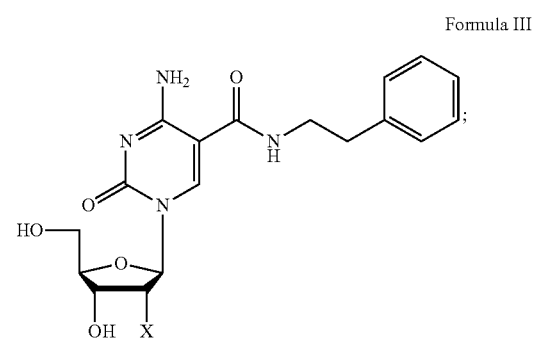

Formula III

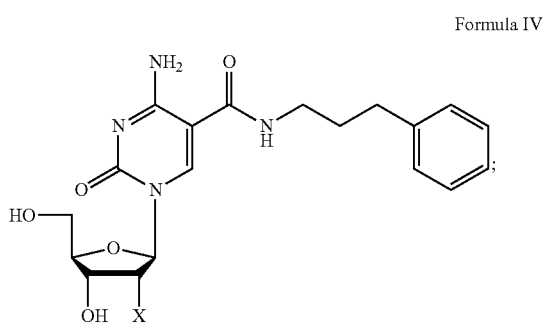

Formula IV

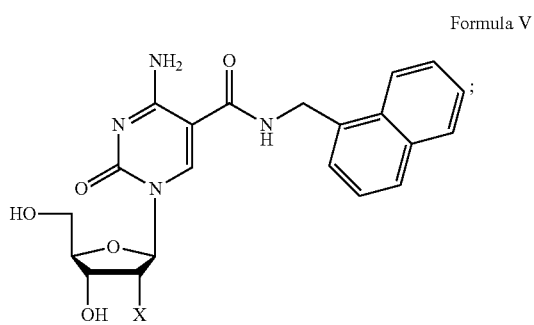

Formula V

-continued

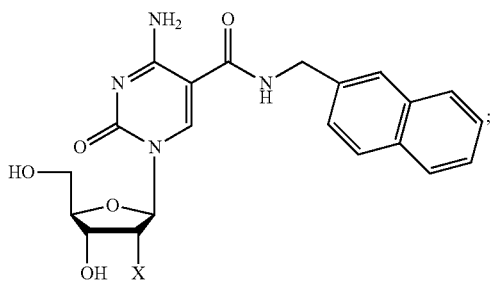

Formula VI

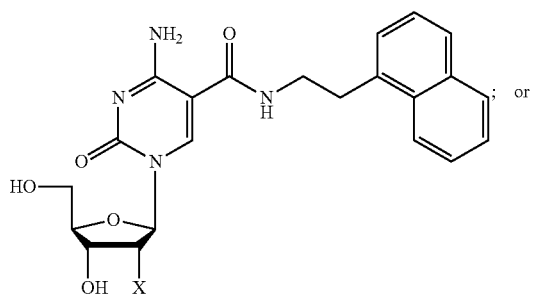

Formula VII

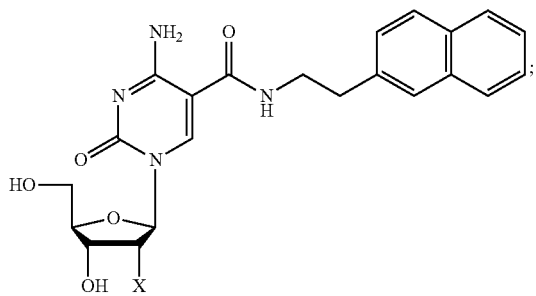

Formula VIII wherein

X is independently selected from the group consisting of —H, —OH, —OMe, —O-allyl, —F, —OEt, —OPr, —OCH$_2$CH$_2$OCH$_3$, NH$_2$ and -azido;

the method comprising synthesizing a nucleic acid molecule having a plurality of nucleotides and at least one compound having the formula selected from the group consisting of Formulas II, III and IV.

As used herein, the term "at least one nucleotide" when referring to modifications of a nucleic acid, refers to one, several, or all nucleotides in the nucleic acid, indicating that any or all occurrences of any or all of A, C, T, G or U in a nucleic acid may be modified or not.

In other aspects, the instant disclosure methods for using the modified nucleosides described herein, either alone or in combination with other modified nucleosides and/or naturally occurring nucleosides, to prepare aptamers and SOMAmers (described herein). In specific embodiments, the aptamers and SOMAmers are prepared using the general SELEX or improved SELEX process as described below.

As used herein, "nucleic acid ligand," "aptamer," "SOMAmer," and "clone" are used interchangeably to refer to a non-naturally occurring nucleic acid that has a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule. In one embodiment, the action is specific binding affinity for a target molecule, such target molecule being a three dimensional chemical structure other than a polynucleotide that binds to the nucleic acid ligand through a mechanism which is independent of Watson/Crick base pairing or triple helix formation, wherein the aptamer is not a nucleic acid having the known physiological function of being bound by the target molecule. Aptamers to a given target include nucleic acids that are identified from a candidate mixture of nucleic acids, where the aptamer is a ligand of the target, by a method comprising: (a) contacting the candidate mixture with the target, wherein nucleic acids having an increased affinity to the target relative to other nucleic acids in the candidate mixture can be partitioned from the remainder of the candidate mixture; (b) partitioning the increased affinity nucleic acids from the remainder of the candidate mixture; and (c) amplifying the increased affinity nucleic acids to yield a ligand-enriched mixture of nucleic acids, whereby aptamers of the target molecule are identified. It is recognized that affinity interactions are a matter of degree; however, in this context, the "specific binding affinity" of an aptamer for its target means that the aptamer binds to its target generally with a much higher degree of affinity than it binds to other, non-target, components in a mixture or sample. An "aptamer," "SOMAmer," or "nucleic acid ligand" is a set of copies of one type or species of nucleic acid molecule that has a particular nucleotide sequence. An aptamer can include any suitable number of nucleotides. "Aptamers" refer to more than one such set of molecules. Different aptamers can have either the same or different numbers of nucleotides. Aptamers may be DNA or RNA and may be single stranded, double stranded, or contain double stranded or triple stranded regions.

As used herein, a "SOMAmer" or Slow Off-Rate Modified Aptamer refers to an aptamer having improved off-rate characteristics. SOMAmers can be generated using the improved SELEX methods described in U.S. Pat. No. 7,947,447, entitled "Method for Generating Aptamers with Improved Off-Rates."

As used herein, "protein" is used synonymously with "peptide," "polypeptide," or "peptide fragment." A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

The SELEX Method

The terms "SELEX" and "SELEX process" are used interchangeably herein to refer generally to a combination of (1) the selection of nucleic acids that interact with a target molecule in a desirable manner, for example binding with high affinity to a protein, with (2) the amplification of those selected nucleic acids. The SELEX process can be used to identify aptamers with high affinity to a specific target molecule or biomarker.

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands." The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-$NH_2$), 2'-fluoro (2'-F), and/or 2'-O-methyl (2'-OMe). See also, U.S. Patent Application Publication No. 20090098549, entitled "SELEX and PHOTOSELEX," which describes nucleic acid libraries having expanded physical and chemical properties and their use in SELEX and photoSELEX.

SELEX can also be used to identify aptamers that have desirable off-rate characteristics. See U.S. Pat. No. 7,947,447, entitled "Method for Generating Aptamers with Improved Off-Rates," which is incorporated herein by reference in its entirety, describes improved SELEX methods for generating aptamers that can bind to target molecules. Methods for producing aptamers and photoaptamers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates dissociate and do not reform, while complexes with slow dissociation rates remain intact. Additionally, the methods include the use of modified nucleotides in the production of candidate nucleic acid mixtures to generate aptamers with improved off-rate performance (see U.S. Pat. No. 8,409,795, entitled "SELEX and PhotoSELEX"). (See also U.S. Pat. No. 7,855,054 and U.S. Patent Publication No. 20070166740). Each of these applications is incorporated herein by reference in its entirety.

"Target" or "target molecule" or "target" refers herein to any compound upon which a nucleic acid can act in a desirable manner. A target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc., without limitation. Virtually any chemical or biological effector may be a suitable target. Molecules of any size can serve as targets. A target can also be modified in certain ways to enhance the likelihood or strength of an interaction between the target and the nucleic acid. A target can also include any minor variation of a particular compound or molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule" or "target" is a set of copies of one type or species of molecule or multimolecular structure that is capable of binding to an aptamer. "Target molecules" or "targets" refer to more than one such set of molecules. Embodiments of the SELEX process in which the target is a peptide are described in U.S. Pat. No. 6,376,190, entitled "Modified SELEX Processes Without Purified Protein."

As used herein, "competitor molecule" and "competitor" are used interchangeably to refer to any molecule that can form a non-specific complex with a non-target molecule. In this context, non-target molecules include free aptamers, where, for example, a competitor can be used to inhibit the aptamer from binding (rebinding), non-specifically, to another non-target molecule. A "competitor molecule" or "competitor" is a set of copies of one type or species of molecule. "Competitor molecules" or "competitors" refer to more than one such set of molecules. Competitor molecules include, but are not limited to oligonucleotides, polyanions (e.g., heparin, herring sperm DNA, salmon sperm DNA, tRNA, dextran sulfate, polydextran, abasic phosphodiester polymers, dNTPs, and pyrophosphate). In various embodiments, a combination of one or more competitor can be used.

As used herein, "non-specific complex" refers to a non-covalent association between two or more molecules other than an aptamer and its target molecule. A non-specific complex represents an interaction between classes of molecules. Non-specific complexes include complexes formed between an aptamer and a non-target molecule, a competitor and a non-target molecule, a competitor and a target molecule, and a target molecule and a non-target molecule.

As used herein, the term "slow off-rate enrichment process" refers to a process of altering the relative concentrations of certain components of a candidate mixture such that the relative concentration of aptamer affinity complexes having slow dissociation rates is increased relative to the concentration of aptamer affinity complexes having faster, less desirable dissociation rates. In one embodiment, the slow off-rate enrichment process is a solution-based slow off-rate enrichment process. In this embodiment, a solution-based slow off-rate enrichment process takes place in solution, such that neither the target nor the nucleic acids forming the aptamer affinity complexes in the mixture are immobilized on a solid support during the slow off-rate enrichment process. In various embodiments, the slow-off rate enrichment process can include one or more steps, including the addition of and incubation with a competitor molecule, dilution of the mixture, or a combination of these (e.g., dilution of the mixture in the presence of a competitor molecule). Because the effect of a slow off-rate enrichment process generally depends upon the differing dissociation rates of different aptamer affinity complexes (i.e., aptamer affinity complexes formed between the target molecule and different nucleic acids in the candidate mixture), the duration of the slow off-rate enrichment process is selected so as to retain a high proportion of aptamer affinity complexes having slow dissociation rates while substantially reducing the number of aptamer affinity complexes having fast dissociation rates. The slow off-rate enrichment process may be used in one or more cycles during the SELEX process. When dilution and the addition of a competitor are used in combination, they may be performed simultaneously or sequentially, in any order. The slow-off rate enrichment process can be used when the total target (protein) concentration in the mixture is low. In one embodiment, when the slow off-rate enrichment process includes dilution, the mixture can be diluted as much as is practical, keeping in mind that the aptamer retained nucleic acids are recovered for subsequent rounds in the SELEX process. In one embodiment, the slow off-rate enrichment process includes the use of a competitor as well as dilution, permitting the mixture to be diluted less than might be necessary without the use of a competitor.

In one embodiment, the slow off-rate enrichment process includes the addition of a competitor, and the competitor is a polyanion (e.g., heparin or dextran sulfate (dextran)). Heparin and dextran have been used in the identification of specific aptamers in prior SELEX selections. In such methods, however, heparin or dextran is present during the equilibration step in which the target and aptamer bind to form complexes. In such methods, as the concentration of heparin or dextran increases, the ratio of high affinity target/aptamer complexes to low affinity target/aptamer complexes increases. However, a high concentration of heparin or dextran can reduce the number of high affinity target/aptamer complexes at equilibrium due to competition for target binding between the nucleic acid and the competitor. By contrast, the presently described methods add the competitor after the target/aptamer complexes have been allowed to form, and therefore does not affect the number of complexes formed. Addition of competitor after equilibrium binding has occurred between target and aptamer creates a non-equilibrium state that evolves in time to a new equilibrium with fewer target/aptamer complexes. Trapping target/aptamer complexes before the new equilibrium has been reached enriches the sample for slow off-rate aptamers since fast off-rate complexes will dissociate first.

In another embodiment, a polyanionic competitor (e.g., dextran sulfate or another polyanionic material) is used in the slow off-rate enrichment process to facilitate the identification of an aptamer that is refractory to the presence of the polyanion. In this context, "polyanionic refractory aptamer" is an aptamer that is capable of forming an aptamer/target complex that is less likely to dissociate in the solution that also contains the polyanionic refractory material than an aptamer/target complex that includes a nonpolyanionic refractory aptamer. In this manner, polyanionic refractory aptamers can be used in the performance of analytical methods to detect the presence or amount or concentration of a target in a sample, where the detection method includes the use of the polyanionic material (e.g. dextran sulfate) to which the aptamer is refractory.

Thus, in one embodiment, a method for producing a polyanionic refractory aptamer is provided. In this embodiment, after contacting a candidate mixture of nucleic acids with the target, the target and the nucleic acids in the candidate mixture are allowed to come to equilibrium. A polyanionic competitor is introduced and allowed to incubate in the solution for a period of time sufficient to insure that most of the fast off rate aptamers in the candidate mixture dissociate from the target molecule. Also, aptamers in the candidate mixture that may dissociate in the presence of the polyanionic competitor will be released from the target molecule. The mixture is partitioned to isolate the high affinity, slow off-rate aptamers that have remained in association with the target molecule and to remove any uncomplexed materials from the solution. The aptamer can then be released from the target molecule and isolated. The isolated aptamer can also be amplified and additional rounds of selection applied to increase the overall performance of the selected aptamers. This process may also be used with a minimal incubation time if the selection of slow off-rate aptamers is not needed for a specific application.

Thus, in one embodiment a modified SELEX process is provided for the identification or production of aptamers having slow (long) off rates wherein the target molecule and candidate mixture are contacted and incubated together for a period of time sufficient for equilibrium binding between the target molecule and nucleic acids contained in the candidate mixture to occur. Following equilibrium binding an excess of competitor molecule, e.g., polyanion competitor, is added to the mixture and the mixture is incubated together with the excess of competitor molecule for a predetermined period of time. A significant proportion of aptamers having off rates that are less than this predetermined incubation period will dissociate from the target during the predetermined incubation period. Re-association of these "fast" off rate aptamers with the target is minimized because of the excess of competitor molecule which can non-specifically bind to the target and occupy target binding sites. A significant proportion of aptamers having longer off rates will remain complexed to the target during the predetermined incubation period. At the end of the incubation period, partitioning nucleic acid-target complexes from the remainder of the mixture allows for the separation of a population of slow off-rate aptamers from those having fast off rates. A dissociation step can be used to dissociate the slow off-rate aptamers from their target and allows for isolation, identification, sequencing, synthesis and amplification of slow off-rate aptamers (either of individual aptamers or of a group of slow off-rate aptamers) that have high affinity and specificity for the target molecule. As with conventional SELEX the aptamer sequences identified from one round of the modified SELEX process can be used in the synthesis of a new candidate mixture such that the steps of contacting, equilibrium binding, addition of competitor molecule, incubation with competitor molecule and partitioning of slow off-rate aptamers can be iterated/repeated as many times as desired.

The combination of allowing equilibrium binding of the candidate mixture with the target prior to addition of competitor, followed by the addition of an excess of competitor and incubation with the competitor for a predetermined period of time allows for the selection of a population of aptamers having off rates that are much greater than those previously achieved.

In order to achieve equilibrium binding, the candidate mixture may be incubated with the target for at least about 5 minutes, or at least about 15 minutes, about 30 minutes, about 45 minutes, about 1 hour, about 2 hours, about 3 hours, about 4 hours, about 5 hours or about 6 hours.

The predetermined incubation period of competitor molecule with the mixture of the candidate mixture and target molecule may be selected as desired, taking account of the factors such as the nature of the target and known off rates (if any) of known aptamers for the target. Predetermined incubation periods may be chosen from: at least about 5 minutes, at least about 10 minutes, at least about 20 minutes, at least about 30 minutes, at least 45 about minutes, at least about 1 hour, at least about 2 hours, at least about 3 hours, at least about 4 hours, at least about 5 hours, at least about 6 hours.

In other embodiments a dilution is used as an off rate enhancement process and incubation of the diluted candidate mixture, target molecule/aptamer complex may be undertaken for a predetermined period of time, which may be chosen from: at least about 5 minutes, at least about 10 minutes, at least about 20 minutes, at least about 30 minutes, at least about 45 minutes, at least about 1 hour, at least about 2 hours, at least about 3 hours, at least about 4 hours, at least about 5 hours, at least about 6 hours.

Embodiments of the present disclosure are concerned with the identification, production, synthesis and use of slow off-rate aptamers. These are aptamers which have a rate of dissociation ($t_{1/2}$) from a non-covalent aptamer-target complex that is higher than that of aptamers normally obtained by conventional SELEX. For a mixture containing non-covalent complexes of aptamer and target, the $t_{1/2}$ represents the time taken for half of the aptamers to dissociate from the aptamer-target complexes. The $t_{1/2}$ of slow dissociation rate aptamers according to the present disclosure is chosen from one of: greater than or equal to about 30 minutes; between about 30 minutes and about 240 minutes; between about 30 minutes to about 60 minutes; between about 60 minutes to about 90 minutes, between about 90 minutes to about 120 minutes; between about 120 minutes to about 150 minutes; between about 150 minutes to about 180 minutes; between about 180 minutes to about 210 minutes; between about 210 minutes to about 240 minutes.

A characterizing feature of an aptamer identified by a SELEX procedure is its high affinity for its target. An aptamer will have a dissociation constant ($k_d$) for its target that is chosen from one of: less than about 1 µM, less than about 100 nM, less than about 10 nM, less than about 1 nM, less than about 100 pM, less than about 10 pM, less than about 1 pM.

Chemical Synthesis

Methods for the chemical synthesis of compounds provided in the present disclosure are described herein. These and/or other well-known methods may be modified and/or adapted in known ways in order to facilitate the synthesis of additional compounds provided in the present disclosure.

With reference to Scheme 1, the present disclosure also provides a method for the synthesis of a 3'-phosporamidite of a C-5 modified aminocarbonylpyrimidine. With reference to Scheme 1, it is worth noting that the palladium catalyzed reaction of carbon monoxide and base with the 5-substituted nucleoside is performed at carbon monoxide pressures less than or equal to 2 atmospheres; more specifically from 0.1 to 2 atmospheres (or 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9 or 2 atmospheres), and even more specifically at 1 atmosphere. Reaction at these reduced pressures leads to higher yields and purer product then previous methods which were performed at pressures between 3 and 4 atmospheres [50 psi].

With reference to Scheme 2, the present disclosure also provides a method for the synthesis of a 5'-triphosphate of a C-5 modified aminocarbonylpyrimidine comprising:

In certain embodiments the protecting group is selected from the group consisting of triphenylmethyl, p-anisyldiphenylmethyl, di-p-anisyldiphenylmethyl, p-dimethoxy trityltrityl, formyl, t-butyloxycarbonyl, benzyloxycarbonyl, 2-chlorobenzyloxycarbonyl, 4-chlorobenzoyloxycarbonyl, 2,4-dichlorobenzyloxycarbonyl, furfurylcarbonyl, t-amyloxycarbonyl, adamantyloxycarbonyl, 2-phenylpropyl-(2)-oxycarbonyl, 2-(4-biphenyl)propyl-(2)-oxycarbonyl, 2-nitrophenylsulfenyl and diphenylphosphinyl.

The following examples are provided to illustrate certain particular features and/or embodiments. These examples should not be construed to limit the disclosure to the particular features or embodiments described.

EXAMPLES

Example 1: Synthesis of 5-(N-benzylcarboxamide)-2'-deoxycytidine

This example provides the methods for making 5-(N-benzylcarboxamide)-2'-deoxycytidine (or BndC; see Scheme 1 (4a) below). In brief, commercially-available 5-iodo-2'-deoxycytidine (3) was converted into the corresponding N-substituted-carboxamide (4a-c) by treatment with the requisite aromatic primary amine $RCH_2NH_2$ (5-10 eq), carbon monoxide (</=1 atm), and $(Ph_3P)_4Pd$ (2 mol %) in N,N-dimethylformamide (DMF) at room temperature for 24-48 hours (Scheme 1). The excess primary amine and limited carbon monoxide were necessary to limit formation of the 2-ketocarboxamide byproducts (see, e.g., Uozumi, Y. et al. (2001) and Takacs et al., 2008). The modified nucleoside products (4a-c) were readily purified by recrystallization from alcohol.

The starting materials: 5-iodo-2'-deoxycytidine; 5-iodo-2'-O-methyl-cytidine; 5-iodo-2'-deoxy-2'-flurocytidine were purchased from ChemGenes Corporation (Wilmington, Mass. 01887, USA) or Thermo Fisher Scientific Inc. (Waltham, Mass. 02454, USA). Carbon monoxide (safety: poison gas) at 99.9% purity was purchased from Specialty Gases of America (Toledo, Ohio 43611, USA). All other reagents were purchased from Sigma-Aldrich (Milwaukee, Wis. 53201, USA) and were used as received.

5-(N-benzylcarboxamide)-2'-deoxycytidine (4a)

An argon-filled 1 L round-bottom flask was charged with: 5-iodo-2'-deoxycytidine (30 g, 85 mmol); benzylamine (109.3 g, 1020 mmol, 12 eq); and anhydrous N,N-dimethylformamide (DMF, 205 mL). The mixture was rapidly magnetically-stirred until all the solids had dissolved. The resulting solution was degassed by two cycles of evacuation to 50 mm and refilling with argon. A mixture of bis(dibenzylidineacetone)palladium(0) (978 mg, 1.7 mmol, 0.02 eq) and triphenylphosphine (1.92 g, 7.3 mmol, 0.086 eq) was added and the resulting fine black suspension was rapidly stirred, evacuated to 50 mm and filled with carbon monoxide (1 atm) from a rubber balloon. The mixture was stirred at room temperature (~20° C.) and periodically refilled with carbon monoxide. After 26 hours, the reaction was found to be complete by tlc analysis (silica gel, eluent: 15% methanol/85% dichloromethane (v/v), $R_f$(SM)=0.3, $R_f$(4a)=0.4). The reaction mixture was diluted with ethyl acetate (205 mL), filtered, and rinsed forward with 65% ethyl acetate/35% DMF (100 mL). The clear green filtrate was concentrated on a rotary evaporator (50-80° C., 1-2 mm) until all the solvents and most of the benzylamine had distilled. The dark orange residue (~75 g) was dissolved in hot abs. ethanol (650 mL) and rapidly hot-filtered to remove a small amount of insoluble flakes (~2 g). The clear filtrate was allowed to cool with slow stirring and the product crystallized as needles. After stirring overnight, the slurry was filtered and the cake washed with ice-cold ethanol (100 mL). After drying in vacuo, the product (4a) was obtained as a white, crystalline solid: 22.0 g, 72% yield. $^1$H NMR (500 MHz, d6-DMSO): δ=8.73 (t, J=5.8 Hz, 1H), 8.42 (s, 1H), 8.06 (bs, 1H), 7.75 (bs, 1H), 7.32 (m, 4H), 7.25 (m, 1H), 6.14 (t, J=6.5 Hz, 1H), 5.24 (d, J=4.4 Hz, 1H), 5.03 (t, J=5.5 Hz, 1H), 4.42 (dd, J=15.4, 7.2 Hz, 1H), 4.41 (dd, J=15.4, 7.3 Hz, 1H), 4.26 (m, J=4.3 Hz, 1H), 3.83 (dd, J=7.9, 4.3 Hz, 1H), 3.64 (m, 1H), 3.58 (m, 1H), 2.19 (m, 2H). $^{13}$C NMR (500 MHz, d6-DMSO): δ=165.88 (1C), 163.97 (1C), 153.99 (1C), 144.26 (1C), 139.64 (1C), 128.80 (2C), 127.60 (2C), 127.30 (1C), 99.20 (1C), 88.08 (1C), 86.29 (1C), 70.44 (1C), 61.50 (1C), 42.72 (1C), 40.62 (1C). MS m/z: [M$^-$] calcd for $C_{17}H_{19}N_4O_5$, 359.36; found, 359.1 (ESI$^-$).

4-N-Acetyl-5-(N-benzylcarboxamide)-2'-deoxycytidine (5a)

A 1 L round bottom flask was charged with (4a) (20.0 g, 55.4 mmol), and anh. tetrahydrofuran (THF, 500 mL). The well-stirred mixture was treated with acetic anhydride (26.4 mL, 277 mmol, 5 eq) and the mixture was heated at 50° C. for 20 h. Tlc analysis of an aliquot (homogenized by dissolving in 50% methanol/50% dichloromethane) showed that the reaction was complete (silica gel, eluent: 15% methanol/85% dichloromethane (v/v), $R_f$(4a)=0.4, $R_f$(5a)=0.6). The slurry was cooled to 5-10° C. for 1 hour, filtered, and washed with cold THF (40 mL). Drying in vacuo afforded the product (5a) as white, crystalline needles, 20.4 g, 91% yield. $^1$H NMR (500 MHz, d6-DMSO): δ=11.35 (s, 1H), 8.98 (t, J=5.7 Hz, 1H), 8.73 (s, 1H), 7.34 (d, J=4.4 Hz, 4H), 7.26 (m, J=4.3 Hz, 1H), 6.10 (t, J=6.1 Hz, 1H), 5.28 (d, J=4.4 Hz, 1H), 5.09 (t, J=5.4 Hz, 1H), 4.44 (dd, J=15.3, 8.1 Hz, 1H), 4.43 (dd, J=15.2, 8.1 Hz, 1H), 4.28 (dt, J=9.8, 4.0 Hz, 1H), 3.91 (dd, J=7.9, 4.0 Hz, 1H), 3.68 (m, 1H), 3.60 (m, 1H), 2.41 (s, 3H), 2.34 (m, 1H), 2.22 (m, 1H). $^{13}$C NMR (500 MHz, d6-DMSO): δ=171.27 (1C), 165.49 (1C), 159.77 (1C), 153.19 (1C), 146.24 (1C), 139.16 (1C), 128.82 (2C), 127.76 (2C), 127.41 (1C), 100.32 (1C), 88.67 (1C), 87.50 (1C), 70.11 (1C), 61.17 (1C), 43.00 (1C), 40.78 (1C), 26.70 (1C). MS m/z: [M$^-$] calcd for $C_{19}H_{21}N_4O_6$, 401.40; found, 401.1 (ESI$^-$).

5'-O-(4,4'-Dimethoxytrityl)-4-N-acetyl-5-(N-benzyl-carboxamide)-2'-deoxycytidine (6a)

A 250 mL round bottom flask was charged with (5a) (4.82 g, 12 mmol) and anhydrous pyridine (40 mL). The resulting colorless solution was magnetically-stirred as 4,4'-dimethoxytrityl chloride (4.47 g, 13.2 mmol, 1.1 eq) was added in five portions over one hour. The orange-yellow solution was stirred for 30 minutes more, quenched with ethanol (4.2 mL, 72 mmol), and concentrated on the rotovap (1-2 mm, ≤35° C.). The resulting sticky orange residue (~13 g) was partitioned with ethyl acetate (100 mL) and cold, saturated aq. sodium bicarbonate (50 mL). The organic layer was dried with sodium sulfate, filtered and concentrated to leave a yellow foam. Purification by flash chromatography (silica gel, eluent: 1% triethylamine/99% ethyl acetate, $R_f$(6a)=0.4) afforded (6a) as a white foam, 6.1 g, 72% yield. $^1$H NMR (500 MHz, d6-DMSO): δ=11.44 (s, 1H), 9.12 (t, J=5.5 Hz, 1H), 8.46 (s, 1H), 7.38 (d, J=7.4 Hz, 2H), 7.25 (m, 12H), 6.84 (m, 4H), 6.10 (t, J=6.1 Hz, 1H), 5.34 (d, J=4.7 Hz, 1H), 4.20 (m, 3H), 4.05 (m, 1H), 3.72 (d, J=1.7 Hz, 6H), 3.41 (dd, J=10.5, 6.0 Hz, 1H), 3.20 (dd, J=10.4, 3.5 Hz, 1H), 2.44 (s, 3H), 2.39 (m, 1H), 2.25 (m, 1H). $^{13}$C NMR (500 MHz, d6-DMSO): δ=171.28 (1C), 165.38 (1C), 159.88 (1C), 158.53 (2C), 153.07 (1C), 146.13 (1C), 145.26 (1C), 138.91 (1C), 136.00 (1C), 135.98 (1C), 130.16 (2C), 130.11 (2C), 128.78 (2C), 128.28 (2C), 128.13 (2C), 127.84 (2C), 127.46 (1C), 127.14 (1C), 113.60 (4C), 100.32 (1C), 88.04 (1C), 86.86 (1C), 86.19 (1C), 70.69 (1C), 60.22 (1C), 55.43 (1C), 55.42 (1C), 43.03 (1C), 40.70 (1C), 26.76 (1C). MS m/z: [M$^-$] calcd for $C_{40}H_{39}N_4O_8$, 703.77; found, 703.2 (ESI$^-$).

5'-O-(4,4'-Dimethoxytrityl)-4-N-acetyl-5-(N-benzyl-carboxamide)-2'-deoxycytidine-3'-O—(N,N-diisopropyl-O-2-cyanoethylphosphoramidite) (7a)

A 250 mL round bottom flask was charged with: (6a) (11.0 g, 15.6 mmol); anhydrous dichloromethane (40 mL); 2-cyanoethyl-N,N,N',N'-tetraisopropylphosphordiamidite (5.9 mL, 18.7 mmol, 1.2 eq); and finally, pyridine trifluoroacetate (3.61 g, 18.7 mmol, 1.2 eq). After 30 min., tlc analysis showed that the reaction was complete (silica gel, 75% ethyl acetate/25% hexanes (v/v), $R_f$(6a)=0.2, $R_f$(7a)=0.7/0.8 [two isomers]). The entire reaction mixture was applied to a silica gel flash column preconditioned with 1% triethylamine/64% ethyl acetate/35% hexanes (until the eluent is basic), then eluted with 65% ethyl acetate/35% hexanes (argon-sparged). The product-containing fractions were protected from air in sealed jars under argon and concentrated to afford (7a) as a colorless foam, 10.8 g, 76% yield. $^1$H NMR (500 MHz, d6-DMSO): δ=11.47 (s, 1H), 9.11 (bs, 1H), 8.57/8.54 (s, 1H), 7.37 (m, 2H), 7.24 (m, 12H), 6.84 (m, 4H), 6.10 (m, 1H), 4.40 (m, 1H), 4.21 (m, 3H), 3.70 (m, 8H), 3.55 (m, 2H), 3.28 (m, 2H), 2.75 (t, J=5.9 Hz, 1H), 2.64 (t, J=5.9 Hz, 1H), 2.55 (m, 1H), 2.42 (m, 4H), 1.11 (m, 9H), 0.98 (d, J=6.8 Hz, 3H). $^{31}$P NMR (500 MHz, d6-DMSO): δ=147.55/147.37 (s, 1P). MS m/z: [M$^-$] calcd for $C_{45}H_{56}N_6O_9P$, 903.99; found, 903.3 (ESI$^-$).

Scheme 1

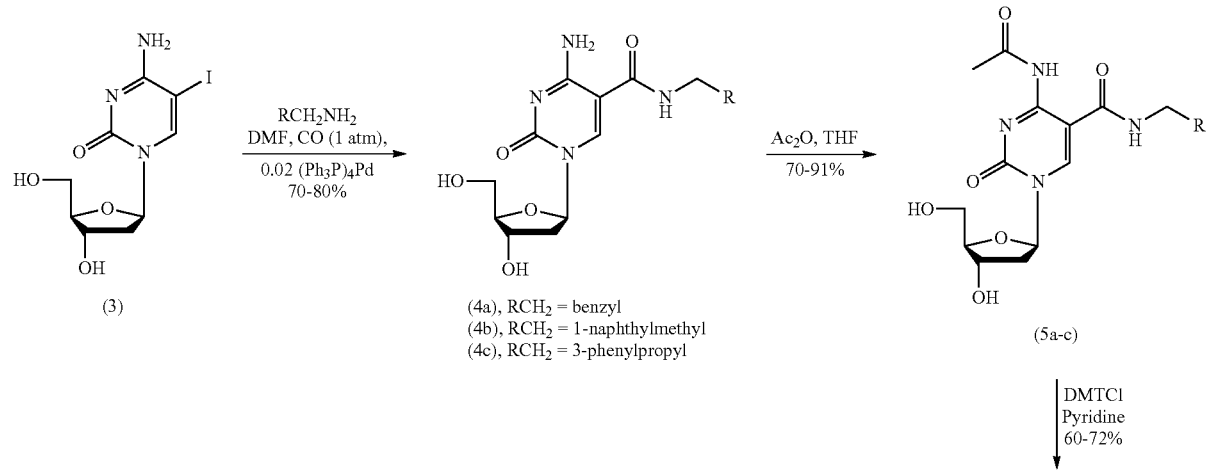

(3)

(4a), RCH$_2$ = benzyl
(4b), RCH$_2$ = 1-naphthylmethyl
(4c), RCH$_2$ = 3-phenylpropyl (5a-c)

DMTCl
Pyridine
60-72%

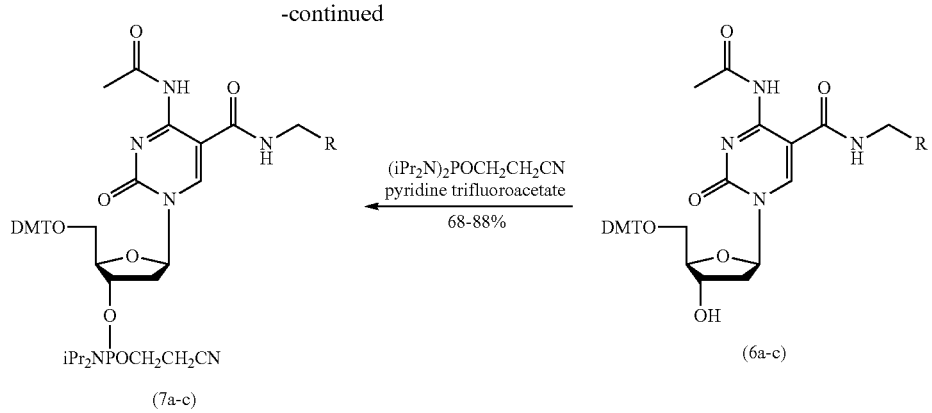

For preparation of 2-cyanoethylphosphoramidite reagents (CEP reagents), the 5-N-benyzlarboxame (4a-c) were selectively N-protected by stirring with acetic anhydride (no base) in tetrahydrofuran (THF), and then 5'-O-protected as the (4,4'-dimethoxytrityl)-derivatives (6a-c) by reaction with 4,4'-dimethoxytrityl chloride in pyridine (see, e.g., Ross et al., 2006). Synthesis of the high purity (>98.0%) CEP reagents (7a-c) was completed by pyridinium trifluoroacetate-catalyzed condensation of the 3'-alcohol with 2-cyanoethyl-N,N,N',N'-tetraisopropyl phosphoramidite (see, e.g., Sanghvi, et al., 2000) and final purification by silica gel flash chromatography with degassed solvents (see, e.g., Still et al., 1978).

For preparation of 5'-triphosphate reagents (TPP reagent; Scheme 2), the 5'-O-DMT-protected nucleosides (6a-c) were peracetylated with acetic anhydride in pyridine, followed by cleavage of the DMT and 4-N-acetyl protecting groups with 1,1,1,3,3,3-hexafluoro-2-propanol (see, e.g., Leonard and Neelima, 1995). The resulting crystalline 3'-O-acetate nucleosides (8a-c) were converted into the crude 5'-O-triphosphates by the Ludwig-Eckstein process. These chemically modified nucleotides generally require a two-stage purification process: anion-exchange chromatography (AEX), followed by reverse phase preparative-HPLC in order to obtain high purity (>%90).

Scheme 2

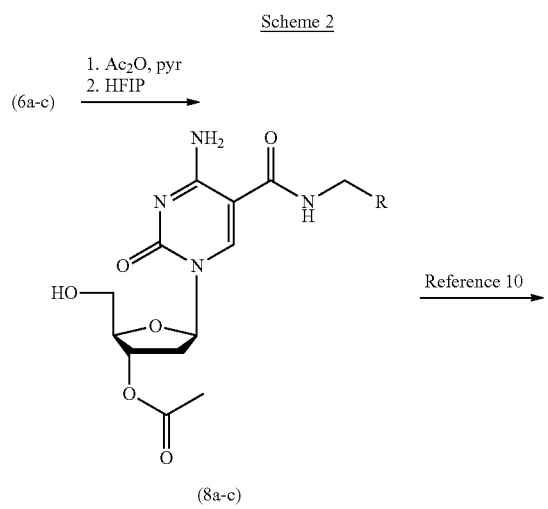

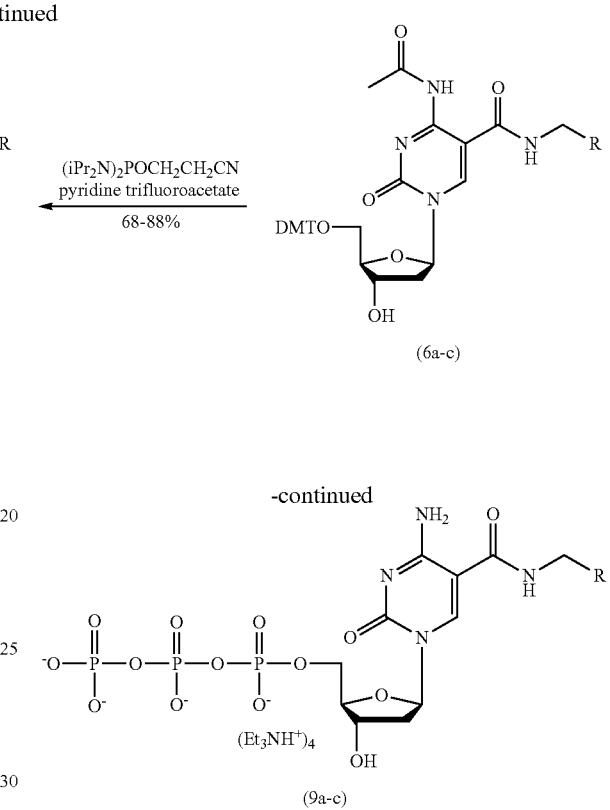

Ludwig, J. and Eckstein, F. (1989) Rapid and Efficient Synthesis of Nucleoside 5'-O-(1-Thiotriphosphates), 5'-Triphosphates and 2',3'-Cyclophosphorothioates Using 2-Chloro-4H-1,3,2-benzodioxaphophorin-4-one. *J. Org. Chem.*, 54, 631-635, which is hereby incorporated by reference in its entirety.

The carboxyamidation reaction was also suitable for preparation of nuclease-resistant ribo-sugar analogues (see, e.g., Ito et al., 2003) (Scheme 4), for example, 5-(N-benzylcarboxamide)-2'-O-methyl-cytidine (12) and -5-(N-3-phenylpropylcarboxamide)-2'-deoxy-2'-fluoro-cytidine (13).

5-(N-Benzylcarboxamide)-2'-O-methyl-cytidine (12)

Prepared from 5-iodo-2'-O-methylcytidine as described for (4a), except that the product was crystallized from hot 2-propanol (12 mL/g) affording (12) as a felty white solid, 79% yield. $^1$H NMR (500 MHz, d6-DMSO): δ=8.57 (t, J=5.9 Hz, 1H), 8.57 (s, 1H), 8.05 (bs, 1H), 7.85 (bs, 1H), 7.33 (m, 4H), 7.25 (m, 1H), 5.85 (d, J=3.1 Hz, 1H), 5.27 (t, J=5.4 Hz, 1H), 5.11 (d, J=6.8 Hz, 1H), 4.43 (dd, J=15.4, 10.4 Hz, 1H), 4.40 (dd, J=15.3, 10.4 Hz, 1H), 4.17 (dd, J=6.7, 5.2 Hz, 1H), 3.87 (dt, J=6.8, 3.2 Hz, 1H), 3.80 (dd, J=5.0, 3.2 Hz, 1H), 3.77 (m, 1H), 3.61 (ddd, J=12.2, 5.3, 3.4 Hz, 1H), 3.44 (s, 3H). $^{13}$C NMR (500 MHz, d6-DMSO): δ=165.43 (1C), 163.57 (1C), 153.49 (1C), 143.99 (1C), 139.16 (1C), 128.40 (2C), 127.22 (2C), 126.90 (1C), 98.97 (1C), 87.95 (1C), 84.28 (1C), 83.05 (1C), 67.67 (1C), 59.92 (1C), 57.70 (1C), 42.40 (1C). MS m/z: [M$^-$] calcd for $C_{18}H_{21}N_4O_6$, 389.39; found, 389.1 (ESI$^-$).

5-(N-3-Phenylpropyl)-2'-deoxy-2'-fluoro-cytidine (13)

Prepared from 5-iodo-2'-deoxy-2'-fluoro-cytidine as described for (4c) as felty white solid (53% yield). $^1$H NMR (500 MHz, d6-DMSO): δ=8.52 (s, 1H), 8.07 (bs, 1H), 7.95 (t, J=5.4 Hz, 1H), 7.85 (bs, 1H), 7.22 (t, J=7.4, 5H), 5.91 (d, J=17.6 Hz, 1H), 5.58 (d, J=6.6 Hz, 1H), 5.32 (t, J=5.3 Hz, 1H), 4.99 (dd, J=53.2, 3.9 Hz, 1H), 4.27 (m, 1H), 3.92 (d, J=8.3 Hz, 1H), 3.86 (m, 1H), 3.58 (ddd, J=12.5, 5.4, 2.9 Hz, 1H), 3.19 (dd, J=12.7, 5.3 Hz, 2H), 2.61 (t, J=7.5 Hz, 2H), 1.78 (m, J=7.3 Hz, 2H). $^{13}$C NMR (500 MHz, d6-DMSO): δ=165.22 (s, 1C), 163.74 (s, 1C), 153.34 (s, 1C), 143.82 (s, 1C), 141.73 (s, 1C), 128.42 (s, 2C), 128.35 (s, 2C), 125.81 (s, 1C), 99.26 (1C), 94.02 (d, J=736.6 Hz, 1C), 88.65 (d, J=134.7 Hz, 1C), 83.07 (s, 1C), 67.00 (d, J=65 Hz, 1C), 59.24 (s, 1C), 38.65 (s, 1C), 32.64 (s, 1C), 30.73 (s, 1C). $^{19}$F NMR (400 MHz, d6-DMSO): δ=−200.82 (ddd, J=19.0, 6.2, 56.6 Hz, 1F). MS m/z: [M$^-$] calcd for $C_{19}H_{22}N_4O_5$, 405.41; found, 405.1 (ESI$^-$).

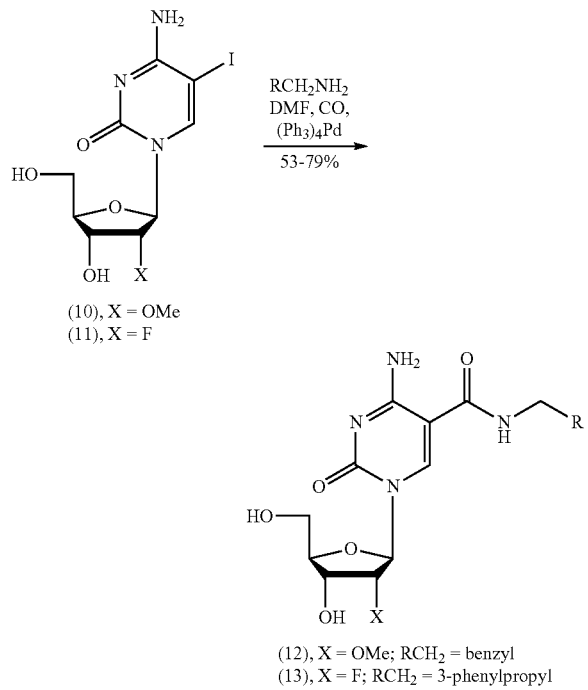

Scheme 3

(10), X = OMe
(11), X = F (12), X = OMe; RCH$_2$ = benzyl
(13), X = F; RCH$_2$ = 3-phenylpropyl The Ludwig-Eckstein process was used to convert the 3'-O-acetyl-protected intermediates (8a-c) into crude 5'-O-triphosphates (9a-c). An alternative two-stage preparative HPLC purification was used for these chemically-modified nucleotides.

3'-O-Acetyl-5-(N-1-benzylcarboxamide)-2'-deoxycytidine (8a)

An argon purged 50 mL round bottom flask was charged with (6a) (900 mg, 1.35 mmol), anh. pyridine (9 mL) and acetic anhydride (0.63 mL, 6.75 mmol). After 18 h at room temperature, the solvent was evaporated in vacuo (1 mm, 30° C.) to yield a tan foam which was dissolved in 1,1,1,3,3,3-hexafluoro-2-propanol (9 mL) and heated at 50° C. under argon. After 6 h, the reaction mixture was poured into a rapidly stirring mixture of methanol (15 mL) and toluene (10 mL). The resulting orange solution was concentrated (1 mm, 30° C.) to yield a red oily residue which, upon mixing with ethyl acetate (6 mL), gave a crystalline slurry. Crystallization was further enhanced with the addition of hexanes (1 mL). The mixture was stirred overnight and filtered, washing the filter cake with 50:50 ethyl acetate:hexanes. The product (8a) was isolated, after drying, as a pale gray solid (405 mg), 75% yield: $^1$H NMR (500 MHz, d6-DMSO): δ=8.82 (t, J=5.8 Hz, 1H), 8.41 (s, 1H), 8.09 (bs, 1H), 7.81 (bs, 1H), 7.33 (m, 4H), 7.25 (m, 1H), 6.17 (dd, J=8.0, 6.0 Hz, 1H), 5.24 (dt, J=6.2, 1.8 Hz, 1H), 5.13 (t, J=5.6 Hz, 1H), 4.43 (dd, J=15.4, 13.3 Hz, 1H), 4.19 (dd, J=15.3, 13.2 Hz, 1H), 4.06 (dd, J=5.9, 3.7 Hz, 1H), 3.65 (m, 2H), 2.45 (m, 1H), 2.34 (ddd, J=14.2, 5.9, 1.5 Hz, 1H), 2.07 (s, 3H). $^{13}$C NMR (500 MHz, d6-DMSO): δ=170.05 (1C), 165.34 (1C), 163.54 (1C), 153.44 (1C), 143.94 (1C), 139.20 (1C), 128.34 (2C), 127.16 (2C), 126.85 (1C), 99.06 (1C), 85.96 (1C), 85.06 (1C), 74.63 (1C), 61.18 (1C), 42.28 (1C), 37.31 (1C), 20.85 (1C). MS m/z: [M$^-$] calcd for $C_{19}H_{21}N_4O_6$, 401.40; found, 401.1 [M$^-$].

3'-O-Acetyl-5-(N-1-naphthylmethylcarboxamide)-2'-deoxycytidine (8b)

Prepared from (6b), as described for (8a), as a pale gray solid, 54% yield: $^1$H NMR (500 MHz, d6-DMSO): δ=8.89 (t, J=5.8 Hz, 1H), 8.44 (s, 1H), 8.14 (d, J=8.4 Hz, 1H), 8.11 (bs, 1H), 7.96 (dd, J=8.6, 1.3 Hz, 1H), 7.86 (dd, J=6.6, 2.8 Hz, 1H), 7.84 (bs, 1H), 7.57 (m, 2H), 7.49 (m, 2H), 6.15 (dd, J=8.2, 6.0 Hz, 1H), 5.23 (dt, J=6.2, 1.9 Hz, 1H), 5.13 (t, J=5.8 Hz, 1H), 4.94 (dd, J=15.5, 5.8 Hz, 1H), 4.86 (dd, J=15.7, 5.4 Hz, 1H), 4.05 (dt, J=8.1, 1.8 Hz, 1H), 3.62 (m, 2H), 2.45 (m, 1H), 2.33 (ddd, J=12.6, 6.1, 1.8 Hz, 1H), 2.06 (s, 3H). $^{13}$C NMR (500 MHz, d6-DMSO): δ=170.51 (1C), 165.78 (1C), 164.02 (1C), 153.90 (1C), 144.52 (1C), 134.57 (1C), 133.74 (1C), 131.27 (1C), 129.02 (1C), 128.03 (1C), 126.80 (1C), 126.31 (1C), 125.94 (1C), 125.54 (1C), 123.78 (1C), 99.52 (1C), 86.60 (1C), 85.55 (1C), 70.12 (1C), 61.67 (1C), 40.80 (1C), 37.75 (1C), 21.32 (1C). MS m/z: [M$^-$] calcd for $C_{23}H_{23}N_4O_6$, 451.46; found, 451.1 (ESI$^-$).

3'-O-Acetyl-5-(N-3-phenylpropylcarboxamide)-2'-deoxycytidine (8c)

Prepared from (6c), as described for (8a), as a white solid, 74% yield: $^1$H NMR (500 MHz, d6-DMSO): δ=8.37 (s, 1H), 8.26 (t, J=5.3 Hz, 1H), 8.06 (bs, 1H), 7.79 (bs, 1H), 7.23 (m, 5H), 6.16 (dd, J=7.9, 6.1 Hz, 1H), 5.24 (dt, J=4.2, 2.1 Hz, 1H), 5.18 (t, J=5.6 Hz, 1H), 4.06 (dd, J=5.7, 3.6 Hz, 1H), 3.65 (m, 2H), 3.19 (dd, J=12.8, 6.2 Hz, 2H), 2.62 (t, J=7.5 Hz, 2H), 2.43 (m, 1H), 2.34 (m, 1H), 2.06 (s, 3H), 1.78 (m, J=7.4 Hz, 2H). $^{13}$C NMR (500 MHz, d6-DMSO): δ=170.52 (1C), 165.68 (1C), 164.00 (1C), 153.94 (1C), 144.09 (1C), 142.13 (1C), 128.80 (2C), 127.75 (2C), 126.21 (1C), 99.80 (1C), 86.42 (1C), 85.06 (1C), 75.07 (1C), 61.63 (1C), 39.12 (1C), 37.91 (1C), 33.04 (1C), 31.18 (1C), 21.31 (1C). MS m/z: [M$^-$] calcd for $C_{21}H_{25}N_4O_6$, 429.45; found, 429.1 (ESI$^-$).

Example 2: Synthesis of 5-(N-1-Napthylmethyl)-2'-deoxycytidine-5-carboxamide

This example provides the methods for making 5-(N-1-Napthylmethyl)-2'-deoxycytidine-5-carboxamide (or NapdC; see Scheme 1 (4b) in Example 1).

The starting materials: 5-iodo-2'-deoxycytidine; 5-iodo-2'-O-methyl-cytidine; 5-iodo-2'-deoxy-2'-flurocytidine were purchased from ChemGenes Corporation (Wilmington, Mass. 01887, USA) or Thermo Fisher Scientific Inc. (Waltham, Mass. 02454, USA). Carbon monoxide (safety: poison gas) at 99.9% purity was purchased from Specialty Gases of America (Toledo, Ohio 43611, USA). All other reagents were purchased from Sigma-Aldrich (Milwaukee, Wis. 53201, USA) and were used as received.

5-(N-1-Napthylmethyl)-2'-deoxycytidine-5-carboxamide (4b)

Prepared as described for (4a), using 1-naphthylmethylamine (6 eq) in place of benzylamine, with a reaction time of 48 hours at room temperature. After concentrating the reaction mixture, the residue was extracted with diisopropyl ether (~40 mL/g) to remove most of the excess 1-naphthylmethylamine. The residue was crystallized from hot methanol (50 mL/g), with hot filtration, to afford the product (4b; Scheme 1; Example 1) as a white solid, 40% yield. $^1$H NMR (500 MHz, d6-DMSO): δ=8.81 (t, J=5.5 Hz, 1H), 8.43 (s, 1H), 8.14 (d, J=4.4, 1H), 8.09 (bs, 1H), 7.96 (m, 1H), 7.79 (m, 1H), 7.75 (bs, 1H), 7.53 (m, 4H), 6.14 (t, J=6.6 Hz, 1H), 5.24 (d, J=4.3 Hz, 1H), 5.01 (t, J=5.6 Hz, 1H), 4.90 (dd, J=15.6, 13.4 Hz, 1H), 4.89 (dd, J=15.5, 13.2 Hz, 1H), 4.26 (m, J=4.1 Hz, 1H), 3.84 (dd, J=8.4, 4.4 Hz, 1H), 3.58 (m, 2H), 2.20 (m, 2H). $^{13}$C NMR (500 MHz, d6-DMSO): δ=165.45 (1C), 163.58 (1C), 153.57 (1C), 143.93 (1C), 136.07 (1C), 134.20 (1C), 133.32 (1C), 128.61 (1C), 127.59 (1C), 126.34 (1C), 125.89 (1C), 125.53 (1C), 125.07 (1C), 123.36 (1C), 98.82 (1C), 87.71 (1C), 85.99 (1C), 70.13 (1C), 61.16 (1C), 42.42 (1C), 40.14 (1C). MS m/z: [M$^-$] calcd for $C_{21}H_{21}N_4O_5$, 409.42; found, 409.1 (ESI$^-$).

4-N-Acetyl-5-(N-1-naphthylmethylcarboxamide)-2'-deoxycytidine (5b)

A 100 mL round bottom flask was charged with (4b) (1.17 g, 2.85 mmol) and anh. tetrahydrofuran (26 mL) and stirred to form a gray-white slurry. Acetic anhydride (1.4 mL, 14.3 mmol, 5 eq) was added to the mixture dropwise while stirring at room temperature. The reaction mixture was stirred and heated to 50° C. for 21 h. An aliquot was pulled for TLC analysis (silica gel, eluent: 10% methanol/90% dichloromethane (v/v), $R_f$(4b)=0.61, $R_f$(5b)=0.12) which indicated that the reaction was complete. The reaction flask was transferred to an ice bath and stirred for >1 h. The mixture was then filtered and the filter cake was rinsed with chilled isopropyl ether. The resulting solids were collected and further evaporated in vacuo to yield fine gray-white crystals (1.01 g, 78.2% yield). $^1$H NMR (500 MHz, d6-DMSO): δ=11.35 (s, 1H), 9.07 (t, J=4.6 Hz, 1H), 8.74 (s, 1H), 8.15 (d, J=8.7 Hz, 1H), 7.96 (m, 1H), 7.87 (m, 1H), 7.53 (m, 4H), 6.11 (t, J=6.2 Hz, 1H), 5.29 (d, J=4.2 Hz, 1H), 5.08 (t, J=5.4 Hz, 1H), 4.92 (dd, J=15.5, 10.1 Hz, 1H), 4.91 (dd, J=15.7, 9.7 Hz, 1H), 4.28 (dt, J=9.4, 3.8 Hz, 1H), 3.92 (dd, J=7.6, 3.9 Hz, 1H), 3.64 (m, 1H), 3.58 (m, 1H), 2.42 (s, 3H), 2.35 (m, 1H), 2.22 (m, 1H). $^{13}$C NMR (500 MHz, d6-DMSO): δ=171.27 (1C), 165.53 (1C), 159.77 (1C), 153.20 (1C), 146.30 (1C), 136.48 (1C), 134.17 (1C), 133.74 (1C), 131.26 (1C), 129.02 (1C), 128.12 (1C), 126.83 (1C), 126.33 (1C), 125.95 (1C), 123.80 (1C), 100.38 (1C), 88.74 (1C), 87.63 (1C), 70.25 (1C), 61.29 (1C), 41.13 (1C), 40.92 (1C), 26.71 (1C). MS m/z: [M$^-$] calcd for $C_{23}H_{23}N_4O_6$, 451.46; found, 451.1 (ESI$^-$).

5'-O-(4,4'-Dimethoxytrityl)-4-N-Acetyl-5-(N-1-naphthylmethylcarboxamide)-2'-deoxycytidine (6b)

Prepared as described for 6b) as a colorless solid in 59% yield. $^1$H NMR (500 MHz, d6-DMSO): δ=11.40 (s, 1H), 9.35 (bt, 1H), 8.48 (s, 1H), 8.02 (m, 1H), 7.96 (m, 1H), 7.86 (d, J=8.4 Hz, 1H), 7.54 (m, 2H), 7.40 (m, 2H), 7.35 (m, 1H), 7.25 (m, 8H), 6.85 (d, J=8.9 Hz, 4H), 6.09 (t, J=6.1 Hz, 1H), 5.32 (d, J=3.7 Hz, 1H), 4.72 (dd, J=14.9, 4.8 Hz, 1H), 4.60 (dd, J=15.1, 3.4 Hz, 1H), 4.16 (dt, J=10.9, 4.7 Hz, 1H), 4.04 (m, 1H), 3.70 (s, 6H), 3.29 (dd, J=10.5, 6.4 Hz, 1H), 3.18 (dd, J=10.4, 7.0 Hz, 1H), 2.43 (s, 3H), 2.38 (m, 1H), 2.26 (m, 1H). $^{13}$C NMR (500 MHz, d6-DMSO): δ=171.25 (1C), 165.37 (1C), 159.88 (1C), 158.52 (1C), 158.54 (1C), 153.03 (1C), 146.32 (1C), 145.31 (1C), 136.05 (1C), 135.97 (1C), 133.92 (1C), 133.74 (1C), 131.22 (1C), 130.20 (2C), 130.11 (2C), 129.05 (1C), 128.30 (2C), 128.15 (2C), 127.16 (1C), 126.81 (1C), 126.33 (1C), 125.85 (1C), 125.80 (1C), 123.65 (1C), 113.61 (4C), 100.49 (1C), 88.12 (1C), 86.79 (1C), 86.17 (1C), 70.59 (1C), 64.40 (1C), 55.41 (2C), 41.01 (1C), 40.70 (1C), 40.82 (1C), 26.76 (1C). MS m/z: [M$^-$] calcd for $C_{44}H_{41}N_4O_8$, 753.83; found, 753.21 (ESI$^-$).

5'-O-(4,4'-Dimethoxytrityl)-4-N-Acetyl-5-(N-1-naphthylmethylcarboxamide)-2'-deoxycytidine-3'-O—(N,N-diisopropyl-O-2-cyanoethylphosphoramidite) (7b)

Prepared as described for (7a) as a white foam (88% yield). $^1$H NMR (500 MHz, d6-DMSO): δ=11.41 (s, 1H), 9.13 (bs, 1H), 8.56/8.54 (s, 1H), 8.01 (m, 1H), 7.95 (m, 1H), 7.85 (m, 1H), 7.53 (m, 2H), 7.37 (m, 2H), 7.24 (m, 9H), 6.83 (m, 4H), 6.06 (m, 1H), 4.66 (m, 2H), 4.39 (m, 1H), 4.16 (m, 1H), 3.68 (m, 8H), 3.52 (m, 2H), 3.28 (m, 1H), 3.20 (m, 1H), 2.74 (t, J=5.8 Hz, 1H), 2.63 (t, J=5.9 Hz, 1H), 2.45 (m, 5H), 1.09 (m, 9H), 0.96 (d, J=6.8 Hz, 3H). $^{31}$P NMR (500 MHz, d6-DMSO): δ=146.93/146.69 (s, 1P). MS m/z: [M$^-$] calcd for $C_{53}H_{58}N_6O_9P$, 954.05; found, 953.3 (ESI$^-$).

Example 3: Synthesis of 5-(N-3-phenylpropylcarboxamide)-2'-deoxycytidine

This example provides the methods for making 5-(N-3-phenylpropylcarboxamide)-2'-deoxycytidine (or PPdC; see Scheme 1 (4c) in Example 1).

The starting materials: 5-iodo-2'-deoxycytidine; 5-iodo-2'-O-methyl-cytidine; 5-iodo-2'-deoxy-2'-flurocytidine were purchased from ChemGenes Corporation (Wilmington, Mass. 01887, USA) or Thermo Fisher Scientific Inc. (Waltham, Mass. 02454, USA). Carbon monoxide (safety: poison gas) at 99.9% purity was purchased from Specialty Gases of America (Toledo, Ohio 43611, USA). All other reagents were purchased from Sigma-Aldrich (Milwaukee, Wis. 53201, USA) and were used as received.

5-(N-3-phenylpropylcarboxamide)-2'-deoxycytidine (4c)

Prepared as described for (4a) (40 nmol scale), using 3-phenylpropylamine (6 eq) in place of benzylamine and a reaction time of 48 hours at room temperature. After removal of the solvents on the rotovap, the residue was triturated with diethyl ether (~30 mL/g) to extract the excess 3-phenylpropylamine and the gummy residue was dissolved in hot ethanol, stirred at room temperature for 18 h, followed by stirring at 0° C. for 1 h. The resulting mixture was filtered and the mother liquor was evaporated resulting in a brown resin. This was dissolved in warm mixture of dichloromethane and water. After standing and stirring at room temperature, white feathery crystals formed in the organic layer, and in the aqueous layer as well. The triphasic mixture was filtered and the filter cake was washed with diethyl ether to afford (4c)

as a fluffy white solid (10.78 g, 69.5% yield). $^1$H NMR (500 MHz, d6-DMSO): δ=8.39 (s, 1H), 8.13 (t, J=5.3 Hz, 1H), 8.05 (bs, 1H), 7.71 (bs, 1H), 7.28 (t, J=7.4, 2H), 7.22 (d, J=7.0, 2H), 7.17 (t, J=7.4, 1H), 6.13 (t, J=6.4 Hz, 1H), 5.22 (d, J=4.3 Hz, 1H), 5.07 (t, J=5.5 Hz, 1H), 4.26 (dt, J=9.4, 4.1 Hz, 1H), 3.83 (dd, J=7.8, 3.9 Hz, 1H), 3.66 (m, 1H), 3.58 (m, 1H), 3.19 (dd, J=12.9, 6.7 Hz, 2H), 2.61 (t, J=7.5 Hz, 2H), 2.19 (m, 2H), 1.78 (m, J=7.4 Hz, 2H). $^{13}$C NMR (500 MHz, d6-DMSO): δ=165.34 (1C), 163.56 (1C), 153.60 (1C), 143.53 (1C), 141.70 (1C), 128.38 (2C), 128.33 (2C), 125.78 (1C), 98.99 (1C), 87.63 (1C), 85.86 (1C), 69.82 (1C), 60.96 (1C), 40.36 (1C), 38.58 (1C), 32.63 (1C), 32.63 (1C). MS m/z: [M$^-$] calcd for $C_{19}H_{23}N_4O_5$, 387.42; found, 387.1 (ESI$^-$).

4-N-Acetyl-5-(N-3-phenylpropyl)carboxamide-2'-deoxycytidine (5c)

A solution of (4c) (10.8 g, 28 mmol) in anh. THF (100 mL) was stirred and treated dropwise with acetic anhydride (3 eq). The solution was stirred for 18 hours at room temperature affording a thin suspension. The mixture was slowly diluted by drop wise addition of diisopropyl ether (35 mL). The solids were isolated by filtration and dried in vacuo to afford (5c) as a white solid (8.44 g, 70.5% yield). $^1$H NMR (400 MHz, d6-DMSO): δ=11.34 (s, 1H), 8.69 (s, 1H), 8.41 (t, J=5.2 Hz, 1H), 7.23 (m, 5H), 6.09 (t, J=6.0 Hz, 1H), 5.15 (bs, 2H), 4.27 (m, 1H), 3.90 (dd, J=9.6, 3.8 Hz, 1H), 3.68 (m, 1H), 3.59 (m, 1H), 3.21 (dd, J=12.3, 7.0 Hz 2H), 2.62 (m, 2H), 2.40 (s, 3H), 2.33 (m, 1H), 2.21 (m, 1H), 1.79 (m, 2H). $^{13}$C NMR (400 MHz, d6-DMSO): δ=171.21 (1C), 165.34 (1C), 159.73 (1C), 153.21 (1C), 146.01 (1C), 142.08 (1C), 128.80 (2C), 128.75 (2C), 126.22 (1C), 99.14 (1C), 88.61 (1C), 87.41 (1C), 69.88 (1C), 61.05 (1C), 41.04 (1C), 39.22 (1C), 33.01 (1C), 30.97 (1C), 26.67 (1C). MS m/z: [M$^-$] calcd for $C_{21}H_{25}N_4O_6$, 429.45; found, 429.1 (ESI$^-$).

5'-O-(4,4'-Dimethoxytrityl)-4-N-acetyl-5-(N-3-phenylpropyl)carboxamide-2'-deoxycytidine (6c)

Prepared from (5c; Scheme 1; Example 1), as described for (6a) in Example 1 as a white foam (64.6% yield). $^1$H NMR (500 MHz, d6-DMSO): δ=11.38 (s, 1H), 8.56 (t, J=5.2 Hz, 1H), 8.37 (s, 1H), 7.35 (d, J=7.4 Hz, 2H), 7.21 (m, 12H), 6.80 (m, 4H), 6.11 (t, J=6.0 Hz, 1H), 5.32 (d, J=4.8 Hz, 1H), 4.16 (dt, J=10.8, 4.7 Hz, 1H), 4.04 (m, 1H), 3.70 (d, J=2.2 Hz, 6H), 3.26 (dd, J=10.6, 6.1 Hz, 1H), 3.21 (dd, J=10.5, 3.3 Hz, 1H), 3.03 (m, 1H), 2.95 (m, 1H), 2.49 (s, 2H), 2.43 (s, 3H), 2.39 (m, 1H), 2.23 (m, 1H), 1.57 (m, 2H). $^{13}$C NMR (500 MHz, d6-DMSO): δ=170.77 (1C), 164.81 (1C), 159.41 (1C), 158.07 (1C), 158.06 (1C), 152.69 (1C), 145.18 (1C), 144.81 (1C), 141.53 (1C), 135.51 (1C), 135.50 (1C), 129.70 (2C), 129.61 (2C), 128.32 (2C), 128.29 (2C), 127.81 (2C), 127.66 (2C), 126.66 (1C), 125.79 (1C), 113.13 (4C), 100.37 (1C), 87.47 (1C), 86.40 (1C), 85.72 (1C), 70.03 (1C), 59.80 (1C), 54.99 (1C), 54.97 (1C), 40.48 (1C), 38.92 (1C), 32.64 (1C) 32.29 (1C), 26.27 (1C). MS m/z: [M$^-$] calcd for $C_{42}H_{43}N_4O_8$, 731.83; found, 731.2 (ESI$^-$).

5'-O-(4,4'-Dimethoxytrityl)-4-N-acetyl-5-(N-3-phenylpropylcarboxamide)-2'-deoxycytidine-3'-O—(N,N-diisopropyl-O-2-cyanoethylphosphoramidite) (7c)

Prepared from (6c; Scheme 1; Example 1), as described for (7a) in Example 1. A 500 mL round bottom flask containing 6c (7.11 g, 9.70 mmol) under an argon atmosphere was charged with anh. dichloromethane (97 mL). Anhydrous N, N-diisopropylethylamine (3.4 mL, 19.4 mmol) was added to the flask, and mixture was chilled to 0° C. while stirring. Over the course of a half hour, 2-cyanoethyldiisopropyl chlorophosphoramidite (2.6 mL, 11.6 mmol) was added dropwise to the rapidly stirring mixture. The mixture was allowed to slowly warm to room temperature while it stirred. After 17 hour, the reaction was sampled for TLC, which showed that the reaction was complete (silica gel; eluent 75% ethyl acetate/25% hexanes (v/v), $R_f$(6c)=0.10, $R_f$(7b)=0.46/0.56 [two isomers]). The reaction mixture was transferred to a 250 mL separatory funnel using toluene and quenched by washing with cold, argon sparged 2% sodium bicarbonate solution (2×, 400 mL/wash). The organic layer was collected and evaporated until the majority of the dichloromethane had been removed. The organic layer was returned to the separatory funnel with chilled argon-sparged toluene and washed with chilled argon-sparged deionized water (2×, 400 mL/wash). The organic layer was then diluted with chilled argon-sparged ethyl acetate and washed with brine (1×, 400 mL). The organic layer was collected, dried over sodium sulfate, filtered and evaporated. The worked-up reaction mixture was dissolved with dichloromethane and loaded onto a pre-conditioned column (prepared as for (6b)) and eluted with chilled, argon sparged mobile phase (80% ethyl acetate/20% hexanes) and product containing fractions were collected in sealed argon-purged bottles to limit product contact with air. Product containing fractions were evaporated at <40° C. to yield a white foam (6.16 g, 68.0% yield). $^1$H NMR (500 MHz, d6-DMSO): δ=11.40 (s, 1H), 8.56 (m, 1H), 8.47/8.43 (s, 1H), 7.35 (m, 2H), 7.20 (m, 12H), 6.80 (m, 4H), 6.08 (m, 1H), 4.40 (m, 1H), 4.18 (m, 1H), 3.70 (m, 8H), 3.53 (m, 2H), 3.30 (m, 2H), 3.00 (m, 2H), 2.75 (t, J=5.9 Hz, 1H), 2.63 (t, J=5.9 Hz, 1H), 2.56 (m, 1H), 2.50 (m, 2H), 2.40 (m, 4H), 1.59 (m, 2H), 1.11 (m, 9H), 0.97 (d, J=6.8 Hz, 3H). $^{31}$P NMR (500 MHz, d6-DMSO): δ=147.60/147.43 (s, 1P) MS m/z: [M$^-$] calcd for $C_{51}H_{60}N_6O_9P$, 932.05; found, 931.4 (ESI Example 4: Nucleoside Triphosphate Purification by Two-Stage Preparative HPLC This example provides the methods for the purification of nucleoside triphosphates.

The crude triphosphates (9a-c) were purified via two orthogonal preparative HPLC techniques: anion exchange chromatography to separate the nucleoside triphosphate from other nucleoside by-products (such as diphosphate and monophosphate) and reversed-phase chromatography to remove residual by-products of reaction reagents.

Anion exchange chromatography was performed in two injections for each 0.5 mmol reaction using an HPLC column packed with Source 15Q resin, eluting with a linear elution gradient of two triethylammonium bicarbonate buffers (Table 1). The desired triphosphate was usually the final material to elute from the column, as a broad peak with 10-12 minutes width on the HPLC chromatogram. Fractions were analyzed and product-containing fractions were combined and evaporated in a Genevac VC 3000D evaporator to produce a colorless to light tan resin. This was reconstituted in deionized water and applied in a single injection for reversed phase purification on a Novapak HRC18 prep column eluting with a linear gradient of acetonitrile in triethylammonium acetate buffer (Table 2). Fractions containing pure triphosphate were combined and evaporated to produce a colorless to light tan resin.

Final pure triphosphates (9a-c) were reconstituted in deionized water for analysis and quantitated using a Hewlett Packard 8452A Diode Array Spectrophotometer at 240 nm (Table 3).

TABLE 1

AEX Purification Conditions

| | |
|---|---|
| HPLC system | Waters 625HPLC/486 detector @ 240 or 278 nm |
| Column | Source 15 Q 196 mL (GE Healthcare PN: 17-1947-05) |
| Mobile Phase | A: 10 mM Triethylammonium bicarbonate/ 10% Acetonitrile, B: 1M Triethylammonium bicarbonate/ 10% Acetonitrile |
| Gradient (% Buffer B) | 5%-70% |
| Run Time; flow rate; fraction size | 50 min; 35 mL/min; 50 mL |
| Analytical Column | Dionex DNA-Pac PA100 column (Thermo Scientific, PN: 043010) |

TABLE 2

RP-HPLC Purification Conditions

| | |
|---|---|
| HPLC system | Waters 625HPLC/486 detector @ 240 nm |
| Column | Waters Novapak HRC18, 19 mm × 300 mm (PN WAT025822) |
| Mobile Phase | A: 100 mM Triethylammonium acetate B: 100% Acetonitrile |
| Gradient (% Buffer B) | 0%-50% |
| Run Time; flow rate; fraction size | 30 min; 12 mL/min; 25 mL |
| Analytical Column | Waters Symmetry column (PN: WAT054215) |

TABLE 3

Triphosphate Yields and Purities

| Triphosphate | Extinction Coefficient (est3b) | Yield μmoles | Yield Percent | Purity: Analytical AEX | Purity: Analytical RP-HPLC |
|---|---|---|---|---|---|
| (9a) | 13,700 cm$^{-1}$ M$^{-1}$ | 43 | 9% | no data | 92.6% |
| (9b) | 20,000 cm$^{-1}$ M$^{-1}$ | 121 | 24% | 95.5% | 98.2% |
| (9c) | 13,700 cm$^{-1}$ M$^{-1}$ | 92 | 18% | 98.3% | 98.2% |

5-(N-1-Benzylcarboxamide)-2'-deoxycytidine-5'-O-triphosphate (9a)

$^1$H NMR (300 MHz, D$_2$O): δ=8.45 (s, 1H), 7.25 (m, 5H), 6.14 (t, J=6.9 Hz, 1H), 4.57 (m, J=2.9 Hz, 1H), 4.43 (dd, J=20.2, 15.4 Hz, 2H), 4.17 (m, 3H), 2.39 (m, 1H), 2.27 (m, 1H). 13C NMR $^{31}$P NMR (300 MHz, D$_2$O): δ=−9.96 (d, J=50.0 Hz, 1P), −11.43 (d, J=50.8 Hz, 1P), −23.24 (t, J=50.5 Hz, 1P MS m/z: [M$^-$] calcd for C$_{17}$H$_{21}$N$_4$O$_{14}$P$_3$, 599.04; found, 599.1 [M$^-$].

5-(N-1-Naphthylmethylcarboxamide)-2'-deoxycytidine-5'-O-triphosphate (9b)

$^1$H NMR (500 MHz, D$_2$O): δ=8.12 (s, 1H), 7.98 (d, J=8.5 Hz, 1H), 7.69 (d, J=8.1 Hz, 1H), 7.58 (m, 1H), 7.40 (m, 1H), 7.33 (m, 1H), 7.24 (m, 1H), 5.87 (t, J=6.7 Hz, 1H), 4.66 (d, J=8.1 Hz, 2H), 4.40 (m, J=3.0 Hz, 1H), 4.04 (m, 3H), 2.21 (ddd, J=14.1, 6.0, 3.4 Hz, 1H), 2.06 (m, 1H). $^{13}$C NMR (500 MHz, D$_2$O): δ=165.95 (s, 1C), 163.15 (s, 1C), 155.22 (s, 1C), 143.33 (s, 1C), 133.35 (s, 1C), 133.17 (s, 2C), 130.55 (s, 2C), 128.66 (s, 1C), 127.84 (s, 1C), 126.65 (s, 1C), 126.13 (s, 1C), 125.64 (s, 1C), 125.12 (s, 1C), 123.11 (s, 1C), 100.55 (s, 1C), 86.88 (s, 1C), 85.87 (d, J=55.95 Hz, 1C), 70.76 (s, 1C), 65.38 (d, J=36 Hz, 1C), 41.19 (s, 1C), 39.61 (m, 1C). $^{31}$P NMR (500 MHz, D$_2$O): δ=−10.99 (d, J=82.4 Hz, 1P), −11.61 (d, J=84.9 Hz, 1P), −23.47 (t, J=83.5 Hz, 1P). MS m/z: [M$^-$] calcd for C$_{21}$H$_{24}$N$_4$O$_{14}$P$_3$, 649.36; found, 649.0 (ESI$^-$).

5-(N-3-Phenylpropylcarboxamide)-2'-deoxycytidine-5'-O-triphosphate (9c)

$^1$H NMR (500 MHz, D$_2$O): δ=8.07 (s, 1H), 7.11 (m, 4H), 6.98 (m, 1H), 6.00 (t, J=6.5 Hz, 1H), 4.44 (m, J=3.0 Hz, 1H), 4.06 (m, 3H), 3.21 (m, 1H), 3.13 (m, 1H), 2.50 (t, J=7.5 Hz, 2H), 3.13 (ddd, J=14.1, 10.9, 3.1 Hz, 1H), 2.13 (m, 1H), 1.76 (m, 2H). $^{13}$C NMR (500 MHz, D$_2$O): δ=165.85 (s, 1C), 163.50 (s, 1C), 155.73 (s, 1C), 142.94 (s, 1C), 142.40 (s, 1C), 128.55 (s, 2C), 128.40 (s, 2C), 125.72 (s, 1C), 101.15 (s, 1C), 86.93 (s, 1C), 85.96 (d, J=55.2 Hz, 1C), 70.90 (s, 1C), 65.38 (d, J=37.6 Hz, 1C), 39.88 (s, 1C), 39.55 (s, 1C), 32.74 (s, 1C), 26.68 (s, 1C). $^{31}$P NMR (500 MHz, D$_2$O): δ=−11.00 (d, J=82.7 Hz, 1P), −11.09 (d, J=85.7 Hz, 1P), −23.53 (t, J=84.3 Hz, 1P). MS m/z: [M$^-$] calcd for C$_{19}$H$_{25}$N$_4$O$_{14}$P$_3$, 627.35; found, 627.0 (ESI$^-$).

Example 5: Solid-Phase Oligonucleotide Synthesis

An ABI 3900 automated DNA synthesizer (Applied Biosystems, Foster City, Calif.) was used with conventional phosphoramidite methods with minor changes to the coupling conditions for modified phosphoramidites (7a-c) (Table 4). Reagent (7a) was used as a 0.1 M solution in dichloromethane/acetonitrile (1/1) and reagents (7b) and (7c) were used as 0.1 M solutions in acetonitrile. Solid support was an ABI style fitted column packed with controlled pore glass (CPG, Prime Synthesis, Aston, Pa.) loaded with 3'-DMT-dT succinate with 1000 Å pore size. Deprotection was accomplished by treatment with 20% diethylamine in acetonitrile followed by gaseous methylamine cleavage and deprotection for 2 hrs at 35° C. Identity and percent full length (% FL) product were determined on an Agilent 1290 Infinity with an Agilent 6130B single quadrupole mass spectrometry detector using an Acquity OST C18 column 1.7 μm 2.1×100 mm (Waters Corp., Milford, Mass.), using a gradient of 0 to 25 percent B in 11 minutes (Buffer A: 100 mM 1,1,1,3,3,3-hexafluoro-2-propanol, 8.6 mM triethylamine, pH 8.25; Buffer B: 10% Buffer A in 90% acetonitrile).

TABLE 4

ABI 3900 Coupling Cycle Parameters (50 nmol scale)

| Step | Operation | Purpose | reps | Reagent | volume, μl | wait, sec |
|---|---|---|---|---|---|---|
| pre | Prep Support | wash | 3 | ACN | 200 | 0 |
| | Prep Support | detritylation | 2 | Deblock | 50 | 0 |
| 1 | Coupling cycle | detritylation | 3 | Deblock | 50 | 3 |
| 2 | Coupling cycle | wash | 1 | ACN | 195 | 0 |
| 3 (ATG) | Coupling cycle | coupling | 2 | Activator, amidite | 36 + 19 | 30 + 175 |
| 3 (7a-c) | Coupling cycle | coupling | 3 | Activator, amidite | 36 + 19 | 60 + 250 |

TABLE 4-continued

ABI 3900 Coupling Cycle Parameters (50 nmol scale)

| Step | Operation | Purpose | reps | Reagent | volume, μl | wait, sec |
|---|---|---|---|---|---|---|
| 4 | Coupling cycle | capping | 1 | Cap A, B | 15 + 15 | 5 |
| 5 | Coupling cycle | oxidation | 1 | oxidizer | 35 | 3 |
| 8 | Coupling cycle | wash | 1 | ACN | 190 | 0 |
| post | Finalize Oligo | detritylation | 2 | Deblock | 140 | 0 |
|  | Finalize Oligo | wash | 4 | ACN | 199 | 0 |
|  | Finalize Oligo | dry support | 1 | ACN; Ar | 199 | 0 |

Key:
ACN Acetonitrile
Deblock 10% Dichloroacetic acid in toluene
Activator 0.3M 5-Benzylmercaptotetrazole and 0.5% N-methylimidazole in ACN
Oxidizer 0.025M Iodine in 44.9% ACN/45% pyridine/10.1% water
Cap A Acetic Anhydride in pyridine and tetrahydrofuran
Cap B 1-Methylimidazole in tetrahydrofuran
Ar Dry argon flush for 20 sec Primer Extension Assay:

The modified nucleoside triphosphates were evaluated as substrates for KOD exonuclease-minus DNA polymerase in a primer extension assay using a standard template that contained all possible triple nucleotide combinations. The template sequence was:

(SEQ ID NO: 1)
5'- TTTTTTTTCTTCTTCTCCTTTCTCTTCCCAAAATCACACGGACCCA

GGGCATTCTAGATATGGTTTACGCTCAAGCGAACTTGCCGTCCTGAGTGT

AAAGAGGGAAAgagggcagggtgtggcatatatat- 3'

(RC70X27.37, TriLink Biotechnologies).

The primer sequence was:

(SEQ ID NO: 2)
5'-atatatatgccacaccctgccctc-3' ((AT)4-5P27, IDT Technologies).

In brief, 10 pmoles of primer were labeled with 10 pmoles of $^{32}$P-ATP at 37° C. for 30 minutes with 3' phosphatase minus T4 polynucleotide Kinase (New England Biolabs) in 7 mM Tris-HCl, pH 7.6 @ 25° C., 10 mM MgCl$_2$, 5 mM dithiothreitol, and purified by passage through two Sephadex G-50 cartridges (GE Healthcare). The 30 μL primer extension reactions contained 120 mM Tris-HCl, pH 7.8, 10 mM KCl, 7 mM MgSO$_4$, 6 mM (NH$_4$)$_2$SO$_4$, 0.001% BSA, 0.1% Triton X-100, 3 pmoles of template, 6 pmoles of primer, and 7.5 Units of KOD exonuclease-minus DNA polymerase (EMD Novagen). The reactions were incubated at 96° C. for 30 seconds and 65° C. for 1 hour in a 96-well plate in an MJ thermocycler (Bio-Rad).

Five μL samples were analyzed on 8% acrylamide, 7 M urea, 1×TBE gels (Life Technologies) and exposed for 1 hour on an imaging plate before scanning in a FujiFilm FLA3000 phosphorimager (GE Healthcare).

Example 6: Synthesis of Nucleic Acid Molecules with Cytidine-5-Carboxamide Modified Nucleotides This example provides the methods for making nucleic acid molecules having cytidine-5-carboxamide modified nucleotides.

The CEP (phosphoramidite) reagents (7a-c; Scheme 1, Example 1) were tested for use solid-phase oligonucleotide synthesis on an automated synthesizer. For each new amidite reagent, six different oligonucleotides varying in length from 34 to 39 nucleotides in length (or 34, 35, 36, 37, 38 or 39 nucleotides in length) were synthesized with an insertion of from 0, 1, 2, 3, 4 or 5 cytidine-5-carboxamide modified nucleotides in consecutive internal positions, based on the model sequence shown below. The "X" in the sequence indicates the location of the cytidine-5-carboxamide modified nucleotides within the sequence.

(SEQ ID NO: 3)
5'- GAGTGACCGTCTGCCTGX$_{0-5}$CAGACGACGAGCGGGA-3'

Table 5 below summarizes the percent yield of the oligonucleotides synthesize with from 0 to 5 cytidine-5-carboxamide modified nucleotides.

TABLE 5

Synthetic DNA sequences Incorporating Modified 2'-Deoxycytidines

| Sequence | | HPLC | LC/MS Data | | |
|---|---|---|---|---|---|
| Cytidine Mod/ (Phosphoramidite) | $X_n$ n = | Data % FL | FL Expected Mass (amu) | FL Observed Mass (amu) | Δ (amu) |
| Benzyl/ | 0 | 65 | 10533.8 | 10531.2 | 2.6 |
| (7a) | 1 | 60 | 10955.1 | 10953.6 | 1.5 |
|  | 2 | 64 | 11376.4 | 11375.4 | 1.0 |
|  | 3 | 65 | 11797.7 | 11797.9 | 0.2 |
|  | 4 | 52 | 12219.0 | 12220.2 | 1.2 |
|  | 5 | 52 | 12640.4 | 12642.5 | 2.1 |
| 1-Naphthylmethyl/ | 0 | 60 | 10533.8 | 10531.3 | 2.5 |
| (7b) | 1 | 67 | 11005.1 | 11003.3 | 1.7 |
|  | 2 | 64 | 11476.4 | 11475.8 | 0.6 |
|  | 3 | 54 | 11947.7 | 11948.2 | 0.5 |
|  | 4 | 47 | 12419.0 | 12420.2 | 1.2 |
|  | 5 | 49 | 12890.3 | 12892.9 | 2.6 |
| 3-Phenylpropyl/ | 0 | 69 | 10533.8 | 10531.3 | 2.4 |
| (7c) | 1 | 59 | 10983.1 | 10981.3 | 1.8 |
|  | 2 | 68 | 11432.5 | 11431.6 | 0.9 |
|  | 3 | 41 | 11881.9 | 11882.0 | 0.1 |
|  | 4 | 42 | 12331.2 | 12332.2 | 1.0 |
|  | 5 | 49 | 12780.6 | 12782.8 | 2.2 |

The results indicate that full-length synthetic yields for 1 to 3 sequential couplings of the modified cytidine phosphoramidites (7a-c) were comparable to unmodified DNA phosphoramidites. Some loss of yield was observed for 4 or 5 sequential couplings of modified cytidines; however significant amounts of full length product were obtained and confirmed in all cases.

Example 7: Incorporation of Triphosphate Reagents (TPP Reagent) of Cytidine-5-Carboxamide Modified Nucleotides by KOD DNA Polymerase This example shows that the cytidine-5-carboxamide modified nucleotides (9a, 9b and 9c of Scheme 2) may be used as substrates by the KOD exonuclease-minus DNA polymerase.

FIG. 1 below shows the results of a primer extension assay. All three modified cytidine triphosphates were incorporated at least as efficiently as natural, unmodified 2'-deoxycytidine in this assay.

In summary, a practical process for synthesizing cytidine-5-carboxamide modified nucleotides as both 5'-O-triphosphates and 3'-O-CEP phosphoramidites provides valuable new reagents for in vitro selection and post-SELEX optimization of aptamers.

Example 8: Selection of Cytidine-5-Carboxamide Modified Nucleotide Aptamers with SELEX This example shows that cytidine-5-carboxamide modified nucleotide aptamers may be selected for binding to a protein target with SELEX. Further, this example shows a comparison of cytidine-5-carboxamide modified nucleotide aptamers derived from SELEX to a specific protein target to uridine-5-carboxamide modified nucleotide aptamers derived from SELEX to the same protein target.

Four different proteins were used as targets for SELEX: PCSK9, PSMA, ERBB2 and ERBB3.

Modified random libraries were enzymatically synthesized using KOD DNA Polymerase using standard oligonucleotide synthesis protocol. The random libraries included a control library labeled as "dC/dT" and contained no C-5 modified nucleotides; a NapdC library, a NapdU (5-[N-(1-naphthylmethyl)carboxamide]-2'-deoxyuridine) library, a PPdC library and a PPdU (5-[N-(phenyl-3-propyl)carboxamide]-2'-deoxyuridine) library. All random libraries were enzymatically synthesized using these same conditions targeting at least 5 nmole final product per library (50-60% yield from starting antisense template). The crude libraries were concentrated using 10 kDa NMW cut-off ultrafiltration centrifugal devices. The concentrated product was spun down to remove any streptavidin (SA) agarose bead using SPIN-X microcentrifuge tubes, and quantified by measuring absorbance at 260 nm and using estimated absorbance coefficient. Each modified sense library was quality controlled for its inability to shift free SA for contamination of biotinylated anti-sense strands and also standard PCR amplification conditions (data not shown).

Recombinant human PCSK9 protein Gln31-Gln692 (75.1 kDa) with C-terminal poly His tag and produced in human 293 (HEK293) cells was obtained from ACRO Biosystems (Cat# PC9-H5223). This protein is glycosylated and autoproteolytically cleaved DTT-reduced protein runs as 20 KDa (prodomain) and 62 kDa (mature secreted protein) polypeptides on SDS-PAGE gel.

Recombinant human PSMA (~110 kDa) was obtained from R&D Systems (Cat#4234-ZN-010) which was CHO-derived Lys44-Ala750 with N-terminal 6×His tag.

Recombinant human ErbB2 protein Thr23-Thr652 (72.4 kDa) with C-terminal poly His tag and produced in human 293 (HEK293) cells was obtained from ACRO Biosystems (Cat# HE2-H5225). As a result of glycosylation, DTT-reduced protein migrates at 90-110 kDa range on SDS-PAGE for this target.

Recombinant human ErbB3 protein Ser20-Thr643 (71.5 kDa) with C-terminal 6×His tag and produced in human 293 (HEK293) cells was obtained from ACRO Biosystems (Cat# ER3-H5223). As a result of glycosylation, DTT-reduced protein migrates at 100-110 kDa range on SDS-PAGE for this target.

All the targets used in SELEX were checked for their purity and partition capture efficiency using magnetic Dynabeads® His-Tag capture beads Life technologies (Cat#10104D). All the targets were efficiently captured using His tag capture beads.

The SELEX protocol (5 mM DxSO4 Kinetic Challenge starting Round 2) was followed for all the selection steps. For round one, 1000 pmole (~$10^{15}$ sequences) random library for each SELEX experiment was used. Targets were at 50 pmole concentration (captured on 500 µg His Capture Beads) and complexes were equilibrated at 37° C. for 1 hr. and then washed several times with 1XSB18, 0.05% TWEEN20. Selected sequences were eluted with 20 mM NaOH, neutralized and PCR amplified using 5' OH primer and 3' biotinylated primer. The amplified double-stranded unmodified DNA was captured on SA magnetic beads, washed and sense DNA was eluted off, and primer extended using modified nucleotides to regenerate enriched modified pool to be used in next round of SELEX experiments.

A total of six selection rounds were completed. In general, samples were at 1 nM protein concentrations as $C_t$ differences for +/−protein selection samples were not improving indicating probably no further enrichment of sequences, SELEX was stopped at Round 6, modified sense eDNA was made for all samples and pool affinities to respective targets were performed. It should be noted that unmodified control DNA enriched libraries were processed in the similar manner to modified libraries, even though PCR amplified and eluted sense DNA strand could be directed used in next SELEX rounds.

The eDNAs were radio-labeled and filter binding assays were performed for all enriched pools and compared with corresponding starting random libraries. Random libraries did not bind to the four protein. Table 6 shows the affinity data results for the four protein targets PCSK9, PSMA, ERBB2 and ERBB3.

TABLE 6

Target Pool Affinity Data After 6 Rounds of SELEX

| Protein Target | Pool Affinity (nM) | | | |
|---|---|---|---|---|
| | NapdC | NapdU | PPdC | PPdU |
| PCSK9 | 1.57 nM | 0.72 nM | 2.44 nM | 1.02 nM |
| PSMA | 0.86 nM | 7.8 nM | 6.32 nM | 6.79 nM |
| ERBB2 | 11.4 nM | 10.2 nM | 71.3 nM | 6.57 nM |
| ERBB3 | 0.25 nM | 0.38 nM | 15.9 nM | 0.3 nM |

As shown in Table 6, the average binding affinity ($K_d$) for a pool of nucleic acid aptamers having at least one C-5 modified cytodine nucleotide that was enriched for binding to the PSMA target protein via SELEX was 0.86 nM (NapdC), compared to 7.8 nM for a pool of nucleic acid aptamers having a NapdU against the same protein; and 6.32 nM (PPdC), compared to 6.79 nM for a pool of nucleic acid aptamers having a PPdU against the same protein. The average binding affinity ($K_d$) for a pool of nucleic acid aptamers having at least one C-5 modified cytodine nucleotide that was enriched for binding to the ERBB3 target protein via SELEX was 0.25 nM (NapdC), compared to 0.38 nM for a pool of nucleic acid aptamers having a NapdU against the same protein.

Further analysis of the SELEX pools of nucleic acid aptamers enriched for binding to the proteins PSCK9, PSMA, ERBB2 and ERBB3 showed that SELEX performed with nucleic acid aptamers having at least one C-5 modified cytodine nucleotide provided a greater number of multicopy (greater than two (2) copies) nucleic acid sequences in comparison to SELEX performed with nucleic acid aptamers having at least one C-5 modified uridine nucleotide. Table 7 below summarizes the differences of SELEX performed with NapdC, NapdU, PPdC and PPdU.

TABLE 7

Number of Multicopy (>2) Sequenes After 6 Rounds of SELEX

| Protein Target | Number of Multicopy (>2) Sequences | | | |
|---|---|---|---|---|
| | NapdC | NapdU | PPdC | PPdU |
| PCSK9 | 151 | 78 | 302 | 46 |
| PSMA | 187 | 143 | 251 | 58 |
| ERBB2 | 52 | 65 | 85 | 40 |
| ERBB3 | 144 | 160 | 94 | 30 |

In general, Table 7 shows that the C-5 modified cytodine nucleotide provides a greater number of sequences having more than two copies in the pool of nucleic acid aptamer sequences enriched for target protein binding via SELEX. Thus, in general, the C-5 modified cytodine nucleotide in SELEX against a protein target provides a greater diversity of multicopy nucleic acid sequences, which consequently provides a greater number of nucleic acid aptamers to select for further characterization and development as a protein binding reagent and/or therapeutic. This benefit C-5 modified cytodine nucleotides is better realized in light of the challenges associated with developing a nucleic acid aptamer for a particular purpose (e.g., protein binder for assays—pull-down assays, protein purification, mass spectroscopy; a reagent tool and/or therapeutic—protein agonists or antagonist). The greater number of multicopy nucleic acid aptamer provides a greater number of sequences that may be screened and further developed for a particular purpose and reduce the failure rate of such development.

REFERENCES

Gold, L. et al. (2010) Aptamer-based proteomic technology for biomarker discovery. PLoS ONE, 5(12), e15004.

Hollenstein, M. (2012) Synthesis of Deoxynucleoside Triphosphates that Include Proline, Urea, or Sulfonamide Groups and Their Polymerase Incorporation into DNA. Chemistry, A European Journal, 18, 13320-13330.

Imaizumi, Y. et al. (2013) Efficacy of Base-Modification on Target Binding of Small Molecule DNA Aptamers. J. Am. Chem. Soc., 135(25), 9412-9419.

Davies, D. R. et al. (2012) Unique motifs and hydrophobic interactions shape the binding of modified DNA ligands to protein targets. PNAS, 190(49), 19971-19976.

Lee, K. Y. et al. (2010) Bioimaging of Nucleolin Aptamer-Containing 5-(N-benzylcarboxamide)-2'-deoxyuridine More Capable of Specific Binding to Targets in Cancer Cells. J. Biomedicine and Biotechnology, article ID 168306, 9 pages.

Kerr, C. E. et al. Synthesis of N,N-Dialkylaniline-2'-deoxyuridine Conjugates for DNA-Mediated Electron Transfer Studies. Nucleosides, Nucleotides & Nucleic Acids, 19(5&6), 851-866.

Gaballah, S. T. et al. (2002) Synthesis of 5-(2,2'-Bipyridyl- and 2,2'-Bipyridinediiumyl)-2'-deoxyuridine Nucleosides: Precursors to Metallo-DNA Conjugates. Nucleosides, Nucleotides & Nucleic Acids 21 (8&9), 547-560.

Vaught, J. D. et al. (2004) T7 RNA Polymerase Transcription with 5-Position Modified UTP Derivatives. J. Am. Chem. Soc., 126, 11231-11237.

Vaught, J. D.; et al. (2010) Expanding the chemistry of DNA for in vitro selection. J. Am. Chem. Soc., 132(12), 4141-4151.

Nomura, Y. et al. (1997) Site-specific introduction of functional groups into phosphodiester oligodeoxynucleotides and their thermal stability and nuclease-resistance properties. Nucleic Acids Res., 25(14), 2784-2791.

Nomura, Y. et al. (1996) Nucleosides and Nucleotides. 161. Incorporation of 5-(N-aminoalkyl)carbamoyl-2'-deoxycytidines into oligodeoxynucleotides by a convenient post-synthetic modification method. Bioorganic & Medicinal Chemistry Letters, 6(23), 2811-2816.

Uozumi, Y. et al. (2001) Double Carbonylation of Aryl Iodides with Primary Amines under Atmospheric Pressure Conditions Using the Pd/Ph$_3$P/DABCO/THF System. J. Org. Chem. 66, 5272-5274.

Takacs, A. et al. (2008) Palladium-catalyzed Aminocarbonylation of Iodoarenes and Iodoalkenes with Aminophosphonate as N-Nucleophile. Tetrahedron. 64, 8726-8730.

Ross, B. S. et al. (2006) Efficient Large-Scale Synthesis of 5'-O-Dimethoxytrityl-N4-Benzoyl-5-methyl-2'-deoxycytidine. Nucleosides, Nucleotides & Nucleic Acids, 25, 765-770.

Sanghvi, Y. S. et al. (2000) Improved Process for the Preparation of Nucleosidic Phosphoramidites Using a Safer and Cheaper Activator. Organic Process Research & Development, 4, 175-181.

Still, W. C. et al. (1978) Rapid Chromatographic Technique for Preparative Separations with Moderate Resolution. J. Org. Chem., 43, 2923-2925.

Leonard, N. J. and Neelima (1995) 1,1,1,3,3,3-Hexafluoro-2-propanol for the Removal of the 4,4'-Dimethoxytrityl Protecting Group from the 5'-Hydroxyl of Acid-Sensitive Nucleosides and Nucleotides. Tetrahedron Letters, 36(43), 7833-7836.

Ludwig, J. and Eckstein, F. (1989) Rapid and Efficient Synthesis of Nucleoside 5'-O-(1-Thiotriphosphates), 5'-Triphosphates and 2',3'-Cyclophosphorothioates Using 2-Chloro-4H-1,3,2-benzodioxaphophorin-4-one. J. Org. Chem., 54, 631-635.

Ito, T. et al. (2003) Synthesis, thermal stability and resistance to enzymatic hydrolysis of the oligonucleotides containing 5-(N-aminohexyl)carbamoyl-2'-O-methyluridines. Nucleic Acids Res., 31(10), 2514-2523.

The invention claimed is:

1. A compound comprising the structure shown in Formula I:

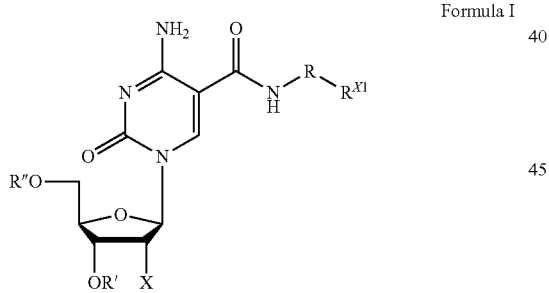

Formula I wherein
R is independently a —(CH$_2$)$_n$—, wherein n is 0, 1, 2, 3, 4, 5, 6, 7, 8, 9 or 10;
R$^{X1}$ comprises

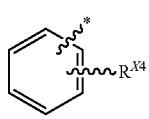

* denotes the point of attachment of the R$^{X1}$ group to the —(CH$_2$)$_n$— group; and
R$^{X4}$ is independently selected from the group consisting of a branched or linear lower alkyl (C1-C20); a hydroxyl group; a halogen (F, Cl, Br, I); nitrile (CN); boronic acid (BO$_2$H$_2$); carboxylic acid (COOH); carboxylic acid ester (COOR$^{X2}$); primary amide (CONH$_2$); secondary amide (CONHR$^{X2}$); tertiary amide (CONR$^{X2}$R$^{X3}$); sulfonamide (SO$_2$NH$_2$); N-alkylsulfonamide (SONHR$^{x2}$);
R$^{X2}$ and R$^{X3}$ are independently, for each occurrence, selected from the group consisting of a branched or linear lower alkyl (C1-C20); phenyl (C$_6$H$_5$); an R$^{X4}$ substituted phenyl ring (R$^{X4}$C$_6$H$_4$), wherein R$^{X4}$ is defined above; a carboxylic acid (COOH); a carboxylic acid ester (COOR$^{X5}$), wherein R$^{X5}$ is a branched or linear lower alkyl (C1-C20); and cycloalkyl, wherein R$^{X2}$=R$^{X3}$=(CH$_2$)$_n$;
X is independently selected from the group consisting of —H, —OH, —OMe, —O-allyl, —F, —OEt, —OPr, —OCH$_2$CH$_2$OCH$_3$ and -azido;
R' is independently selected from the group consisting of a —H, —OAc; —OBz; —P(NiPr$_2$)(OCH$_2$CH$_2$CN); and —OSiMe$_2$tBu;
R" is independently selected from the group consisting of a hydrogen, 4,4'-dimethoxytrityl (DMT) and triphosphate (—P(O)(OH)—O—P(O)(OH)—O—P(O)(OH)$_2$) or a salt thereof;
and salts thereof.

2. The compound of claim 1, wherein R$^{X4}$ is independently selected from the group consisting of a branched or linear lower alkyl (C1-C6); a —OH; a —F and carboxylic acid (COOH).

3. The compound of claim 1, wherein X is independently selected from the group consisting of —H, —OH, —OMe and —F.

4. The compound of claim 1, wherein R' is selected from the group consisting of a —H, —OAc and —P(NiPr$_2$)(OCH$_2$CH$_2$CN).

5. The compound of claim 1, R" is a triphosphate (—P(O)(OH)—O—P(O)(OH)—O—P(O)(OH)$_2$).

6. The compound of claim 1, wherein n is 0, 1, 2 or 3.

7. A nucleic acid molecule comprising the compound of claim 1.

8. A method for making a compound having Formula I:

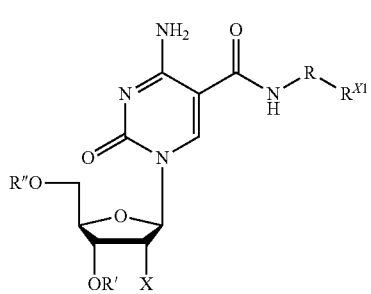

Formula I wherein
R is independently a —(CH$_2$)$_n$—, wherein n is 0, 1, 2, 3, 4, 5, 6, 7, 8, 9 or 10;
R$^{X1}$ comprises

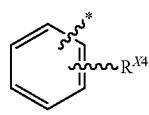

* denotes the point of attachment of the R$^{X1}$ group to the —(CH$_2$)$_n$— group;
R$^{X4}$ is independently selected from the group consisting of a branched or linear lower alkyl (C1-C20); a hydroxyl group; halogen (F, Cl, Br, I); nitrile (CN); boronic acid (BO$_2$H$_2$); carboxylic acid (COOH); carboxylic acid ester (COOR$^{X2}$); primary amide (CONH$_2$); secondary amide (CONHR$^{X2}$); tertiary amide (CONR$^{X2}$R$^{X3}$); sulfonamide (SO$_2$NH$_2$); N-alkylsulfonamide (SONHR$^{X2}$);
R$^{X2}$ and R$^{X3}$ are independently, for each occurrence, selected from the group consisting of a branched or linear lower alkyl (C1-C20); phenyl (C$_6$H$_5$); an R$^{X4}$ substituted phenyl ring (R$^{X4}$C$_6$H$_4$), wherein R$^{X4}$ is defined above; a carboxylic acid (COOH); a carboxylic acid ester (COOR$^{X5}$), wherein R$^{X5}$ is a branched or linear lower alkyl (C1-C20); and cycloalkyl, wherein R$^{X2}$=R$^{X3}$=(CH$_2$)$_n$;
X is independently selected from the group consisting of —H, —OH, —OMe, —O-allyl, —F, —OEt, —OPr, —OCH$_2$CH$_2$OCH$_3$ and -azido;
R' is independently selected from the group consisting of a —H, —OAc; —OBz; —P(NiPr$_2$)(OCH$_2$CH$_2$CN); and —OSiMe$_2$tBu;
R" is independently selected from the group consisting of an hydrogen, 4,4'-dimethoxytrityl (DMT) and triphosphate (—P(O)(OH)—O—P(O)(OH)—O—P(O)(OH)$_2$) or a salt thereof;
the method comprising providing a compound having Formula IX

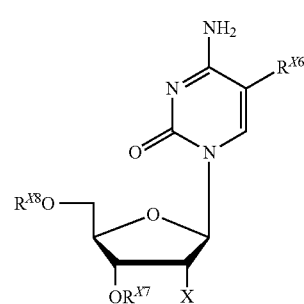

Formula IX wherein,
R$^{X6}$ is an iodine or bromine group;
R$^{X7}$ and R$^{X8}$ are independently, for each occurrence, a hydrogen or protecting group;
X is independently selected from the group consisting of —H, —OH, —OMe, —O-allyl, —F, —OEt, —OPr, —OCH$_2$CH$_2$OCH$_3$ and -azido; and
transforming the compound having Formula IX by a palladium(0) catalyzed reaction in the presence of R$^{X1}$—R—NH$_2$, carbon monoxide and a solvent; and isolating the compound having Formula I.

9. The method of claim 8, wherein R$^{X4}$ is independently selected from the group consisting of a branched or linear lower alkyl (C1-C6); a —OH; a —F and carboxylic acid (COOH).

10. The method of claim 8, wherein R' is selected from the group consisting of a —H, —OAc and —P(NiPr$_2$)(OCH$_2$CH$_2$CN).

11. The method of claim 8, R" is a hydrogen or triphosphate (—P(O)(OH)—O—P(O)(OH)—O—P(O)(OH)$_2$); or salt thereof.

12. The method of claim 8, wherein n is 1, 2 or 3.

13. The method of claim 8, wherein the protecting group is selected from the group consisting of triphenylmethyl, p-anisyldiphenylmethyl, di-p-anisyldiphenylmethyl, p-dimethoxy trityltrityl, formyl, t-butyloxycarbonyl, benzyloxycarbonyl, 2-chlorobenzyloxycarbonyl, 4-chlorobenzoyloxycarbonyl, 2,4-dichlorobenzyloxycarbonyl, furfurylcarbonyl, t-amyloxycarbonyl, adamantyloxycarbonyl, 2-phenylpropyl-(2)-oxycarbonyl, 2-(4-biphenyl)propyl-(2)-oxycarbonyl, 2-nitrophenylsulfenyl and diphenylphosphinyl.

* * * * *

UNITED STATES PATENT AND TRADEMARK OFFICE
CERTIFICATE OF CORRECTION

PATENT NO. : 9,938,314 B2  
APPLICATION NO. : 14/917056  
DATED : April 10, 2018  
INVENTOR(S) : John Rohloff et al.

Page 1 of 1

It is certified that error appears in the above-identified patent and that said Letters Patent is hereby corrected as shown below:

In the Claims

Column 53, Lines 55-63 -- " 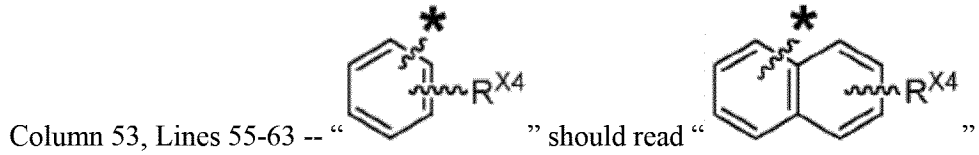 " should read " "

Signed and Sealed this  
Twenty-eighth Day of August, 2018

Andrei Iancu  
*Director of the United States Patent and Trademark Office*

SEQUENCE LISTING

<160> NUMBER OF SEQ ID NOS: 3

<210> SEQ ID NO 1
<211> LENGTH: 131
<212> TYPE: DNA
<213> ORGANISM: Artificial Sequence
<220> FEATURE:
<223> OTHER INFORMATION: synthetic

```
<400> SEQUENCE: 1 tttttttct  tcttctcctt  tctcttccca  aaatcacacg  gacccagggc  attctagata     60
tggtttacgc  tcaagcgaac  ttgccgtcct  gagtgtaaag  agggaaagag  ggcagggtgt   120
ggcatatata  t                                                           131

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
atatatatgc  cacaccctgc  cctc                                             24

<210> SEQ ID NO 3
<211> LENGTH: 38
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (18)..(22)
<223> OTHER INFORMATION: cytidine-5-carboxamide modified nucleotides,
      these nucleotides may be absent.

<400> SEQUENCE: 3
gagtgaccgt  ctgcctgnnn  nncagacgac  gagcggga                             38
```